(12) United States Patent
Kim

(10) Patent No.: US 8,980,917 B2
(45) Date of Patent: Mar. 17, 2015

(54) METHODS FOR TREATING OR PREVENTING BRAIN INFECTIONS

(75) Inventor: Kwang Sik Kim, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 524 days.

(21) Appl. No.: 12/997,763

(22) PCT Filed: Jun. 12, 2009

(86) PCT No.: PCT/US2009/047242
§ 371 (c)(1),
(2), (4) Date: Dec. 13, 2010

(87) PCT Pub. No.: WO2009/152454
PCT Pub. Date: Dec. 17, 2009

(65) Prior Publication Data
US 2011/0098333 A1 Apr. 28, 2011

Related U.S. Application Data

(60) Provisional application No. 61/131,755, filed on Jun. 12, 2008.

(51) Int. Cl.
*A61K 31/47* (2006.01)
*A61K 31/00* (2006.01)
(52) U.S. Cl.
CPC .................. *A61K 31/00* (2013.01); *A61K 31/47* (2013.01)
USPC ........................................................ 514/311
(58) Field of Classification Search
CPC ....................................................... A61K 31/47
USPC ........................................................... 514/311
See application file for complete search history.

(56) References Cited

U.S. PATENT DOCUMENTS

2004/0259863 A1\* 12/2004 Eggenweiler et al. ...... 514/223.8
2007/0032450 A1\* 2/2007 Rieger ............................ 514/45
2007/0066649 A1 3/2007 Nozaki

OTHER PUBLICATIONS

Das et al. "Differential role of cytosolic phospholipase A2 in the invasion of brain microvascular endothelial cells by *Escherichia coli* and *Listeria monocytogenes*." Jour Infect Disease, Sep. 15, 2001, vol. 184, No. 6, pp. 732-737. Especially p. 731 left col. para 1, p. 733 left col. para 4 and right col. para 3, p. 734 fig 3, p. 735 right col. para 2.
Chen et al. "*Cryptococcus neoformans* induces alterations in the cytoskeleton of human brain microvascular endothelial cells". Jour Med Microbiol, Nov. 2003, vol. 52 Part 11, pp. 961-970.
Araseth et al. "CD4 lymphocyte count in HIV-positive persons exposed to *Cryptococcus neformans*." Zentralbl Bakteriol, Nov. 1995, vol. 283, No. 1, pp. 127-135.
Kim, Kwang Sik, "Pathogenesis of Bacterial Meningitis: From Bacteraemia to Neuronal Injury," Nature Reviews, May 2003, vol. 4, pp. 376-385.

(Continued)

*Primary Examiner* — Shengjun Wang
(74) *Attorney, Agent, or Firm* — Venable LLP; Stefan J. Kirchanski

(57) ABSTRACT

The invention is directed to methods of treating organ specific infections in a host organism by administering compounds that target host receptors and/or host cellular signaling molecules to prevent a pathogen from infecting the organ. For example, the administration of a compound to prevent a pathogen from crossing the blood-brain barrier to prevent a brain infection.

7 Claims, 17 Drawing Sheets

(56) References Cited

OTHER PUBLICATIONS

Kim, Kwang Sik, "Mechanisms of microbial traversal of the blood-brain barrier," Nature Reviews, Aug. 2008, vol. 6, pp. 625-634.

Chung et al., 37 kDa laminin receptor precursor modulates cytotoxic necrotizing factor 1-mediated RhoA activation and bacterial uptake. J Biol Chem 278:16857-16862, 2003.

Khan et al., Cytotoxic necrotizing factor-1 contributes to *Escherichia coli* K1 invasion of the central nervous system. J Biol Chem 2002; 277:5607-5612.

Kim KS. *Escherichia coli* translocation at the blood-brain barrier. Infect Immun 2001; 69:5217-5222.

Kim et al., 2008. Ca2+/Calmodulin-dependent invasion of the human brain microvascular endothelial cells by *Escherichia coli* K1. Cell & Tissue Res 332:427-433.

Prasadarao et al., Endothelial cell G1cNAcB1-4 GIcNAc epitopes for outer membrane protein A traversal of *E. coli* across the blood-brain barrier. Infect Immun 1996; 64:154-160.

Shin et al., RhoA and RacI contribute to type III group B streptococcal invasion of human brain microvascular endothelial cells. Biochem Biophys Res Commun 345:538-542, 2006.

Shin et al., Focal adhesion kinase is involved in type III group B streptococcal invasion of human brain microvascular endothelial cells. Microb Pathogenesis 41:168-173, 2006.

* cited by examiner

METHODS FOR TREATING OR PREVENTING BRAIN INFECTIONS

This application is a U.S. National Stage Application of Application No. PCT/US2009/047242, filed Jun. 12, 2009, which claims priority to U.S. Provisional Application No. 61/131,755, filed Jun. 12, 2008, each of which is incorporated by reference in its entirety.

This application claims priority to U.S. Appl. No. 61/131, 755, filed Jun. 12, 2008, the contents of which are incorporated by reference in their entirety.

This invention was made with U.S. Government support of grant number R01-NS26310 awarded by the National Institutes of Health. The Government has certain rights in this invention.

BACKGROUND

Traditional approaches to organ specific infections, for example brain infections, have focused on therapies that eliminate or inactivate the pathogen responsible for the infection. However, the mortality and morbidity associated with brain infections, such as those caused by neonatal bacterial meningitis, have remained significant despite advances in antimicrobial chemotherapy and supportive care. Inadequate knowledge of the pathogenesis has contributed to this high mortality and morbidity (15-17). *E. coli* is the most common gram-negative organism that causes neonatal meningitis. Most cases of neonatal *E. coli* meningitis develop as a result of hematogenous spread, but the microbial-host interactions contributing to *E. coli* meningitis remain incompletely understood (15-17). Other common causes include Group B *Streptococcus* (GBS) for neonatal meningitis and *C. neoformans* infections for immunocompromised patients such as AIDS. There is a need for new therapies that can effectively control infections like meningitis using different therapeutic approaches.

SUMMARY

The invention is directed to methods of treating or preventing meningitis in a subject in need thereof involving the administration of a therapeutic amount of a compound that inhibits at least one cellular signaling molecule selected from the group consisting of phospholipase A2, 5-LO, FLAP, and leukotrienes. In some embodiments, the compound is a 5-LO inhibitor, a FLAP inhibitor, and a CysLT receptor antagonist.

Embodiments of the invention are also directed to methods for preventing meningitis from crossing the blood brain barrier in a subject involving the administration of a therapeutic amount of a compound that inhibits at least one cellular signaling molecule selected from the group consisting of phospholipase A2, 5-LO, FLAP, and leukotrienes to a subject in need thereof. In some embodiments, the compound is a 5-LO inhibitor, a FLAP inhibitor, and a CysLT receptor antagonist.

DETAILED DESCRIPTION

Figure 1:
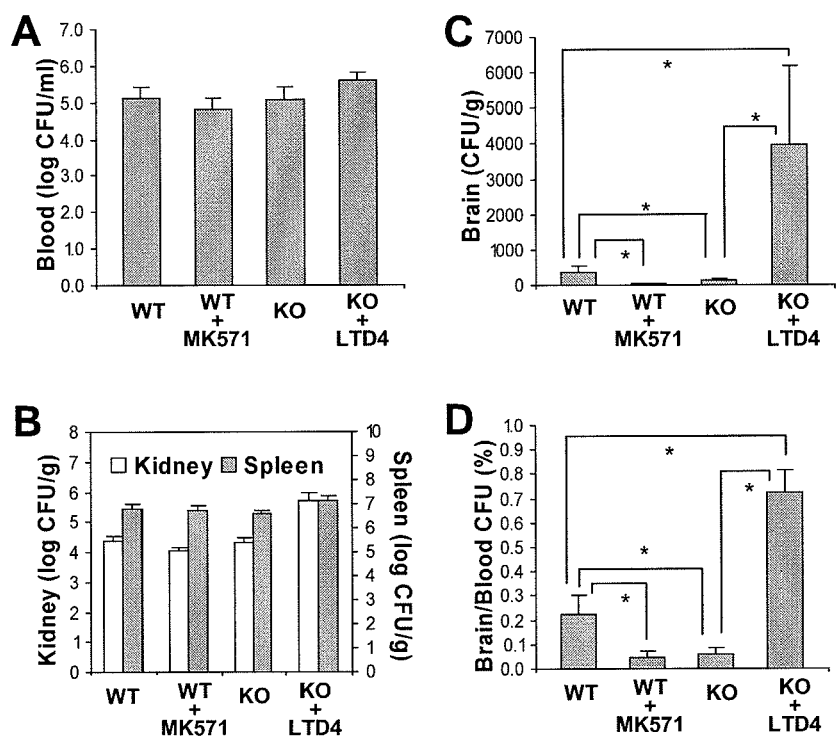
FIG. 1 shows *E. coli* K1 penetration into the brain was significantly less in 5-LO knockout mice (KO) compared to their wild type mice (WT). MK571 significantly inhibited *E. coli* penetration into the brains of wild type mice, while LTD4 rescued the decreased *E. coli* penetration into the brains of 5-LO$^{-/-}$ mice. Bacterial counts in blood (CFU/ml) (A), kidneys and spleens (CFU/gm) (B), brains (CFU/gm) (C), and the percent of brain CFU/blood CFU (D) were determined one hour after intravenous injection of *E. coli* K1 strain RS218. Data shown are mean±SEM. *P value<0.05 compared between WT (n=7) vs WT+MK571 (n=5), or KO (n=7).

Most therapeutic treatments for pathogen based infections, such as meningitis, involve identifying ways to destroy or disrupt the pathogen itself. These methods do not look at ways to disrupt normal cellular signaling processes within the host that would prevent the pathogen from causing infection.

Embodiments of the invention described herein, however, are directed to methods of treating organ specific infections by targeting host receptors or host cellular signaling molecules that, when interrupted, prevent microbes or other infections agents from entering the organ.

For example, compounds can be administered to a person or other mammal with an infections disease to interfere with the pathogen's ability to cross the blood brain barrier. This mechanism can vary depending on host organism and the pathogen but the compounds administered can prevent cellular signaling mechanisms that traditionally permit the pathogen to enter the organ.

In some embodiments, the invention can involve administering an effective amount of a compound to a mammal to interfere with the ability of a pathogen to cross the blood brain barrier. As one of skill in the art can appreciate an "effective amount" or its synonym a "therapeutic amount" is an amount sufficient to prevent the pathogen from entering the organ, for example the brain, in a quantity that causes an infection. In some embodiments, an effective amount can be a dose of between 0.1 mg/kg to about 100 mg/kg administered to a person or other mammal in need thereof.

As the data below indicate, interfering with the mechanisms by which pathogens cross the blood-brain barrier can be accomplished by administering compounds that inhibit, antagonize, or otherwise react with host receptors and/or host signaling molecules to prevent the pathogen from entering the desired organ in an amount sufficient to cause an infection. In some embodiments, the compound can be a 5-LO inhibitor, a FLAP inhibitor, and/or a CysLT receptor antagonist. This mechanism has been shown effective for preventing *E. coli* meningitis as well as *C. neoformans* and GBS penetration.

In some embodiments, the host cellular signaling molecule target can be phospholipase A2, 5-LO, FLAP, and/or leukotrienes. In some embodiments, the phospholipase A2 molecule is a group IV cPLA2. In some embodiments, the leukotriene molecule is LTC4, LTD4, or LTE4.

The methods of the invention can be used to treat organ specific infections. The receptors and cellular signaling molecules in each organ that relate to pathogen entry into the organ are identified and then targeted with appropriate compounds. For example, the methods can be effective in treating and/or preventing meningitis, for example, meningitis that is cerebrospinal fluid culture positive. Example forms of culture positive meningitis include, but are not limited to, *Cryptoccous neoformans*, *E. coli* or group B *Streptococcus*.

A wide array of patients can benefit from the methods disclosed herein. Persons or other mammals suffering from meningitis, tuberculosis, *Streptococcus pneumoniae*, *Neisseria meningitidis*, or cerebral malaria can benefit from treatment using the methods disclosed herein.

Some embodiments of the invention are directed to those patients who are immuno-compromised or lack a sufficiently developed immune system. Such patients can included, but are not limited to, persons with HIV or AIDS, infants and other children, or the elderly. In some embodiments, the patient has a CD4+ T cell count of less than 50 per µl.

The methods used herein can also be used in combination with other therapeutics. As discussed above, the invention herein targets host cellular receptors and host cellular signaling molecules to prevent or treat organ infections. The methods can also be used in conjunction with more traditional therapies designed to kill or inactivate the pathogen itself.

For example, for a person infected with a bacteria the present methods can be used to prevent the pathogen from entering the brain in combination with an antibiotic that would kill the bacteria. Thus the compound administered as part of the invention herein can be combined in a treatment regimen that includes antibiotics, anti-malarial compounds, or other pathogen targeting drugs. These combination regimens can be administered using one of more dosage forms either contemporaneously or at different times.

The methods of the invention can involve administering pharmaceutical compositions that are useful in the methods herein prepared with a therapeutically effective amount of a compound of the invention, as defined herein, and a pharmaceutically acceptable carrier or diluent.

The compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Suitable oral forms for administering the compounds include, lozenges, troches, tablets, capsules, effervescent tablets, orally disintegrating tablets, floating tablets designed to increase gastric retention times, buccal patches, and sublingual tablets.

The compounds of the invention may be systemically administered, e.g., orally, in combination with a pharmaceutically acceptable vehicle such as an inert diluent or an assimilable edible carrier, or by inhalation or insufflation. They may be enclosed in coated or uncoated hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. For compositions suitable for administration to humans, the team "excipient" is meant to include, but is not limited to, those ingredients described in Remington: The Science and Practice of Pharmacy, Lippincott Williams & Wilkins, 21st ed. (2006) (hereinafter Remington's), which is herein incorporated by reference in its entirety.

The compounds may be combined with a fine inert powdered carrier and inhaled by the subject or insufflated. Such compositions and preparations should contain at least 0.01% compounds. The percentage of the compositions and preparations may, of course, be varied and may conveniently be between about 2% to about 60% of the weight of a given unit dosage form. The amount of compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. A syrup or elixir may contain the active compound, sucrose or fructose as a sweetening agent, methyl and propylparabens as preservatives, a dye and flavoring such as cherry or orange flavor.

Various other materials may be present as coatings or to otherwise modify the physical form of the solid unit dosage form. For instance, tablets, pills, or capsules may be coated with gelatin, wax, shellac or sugar and the like. Of course, any material used in preparing any unit dosage form should be pharmaceutically acceptable and substantially non-toxic in the amounts employed.

In addition, the compounds may be incorporated into sustained-release preparations and devices. For example, the compounds may be incorporated into time release capsules, time release tablets, and time release pills. In some embodiments, the composition is administered using a dosage form selected from the group consisting of effervescent tablets, orally disintegrating tablets, floating tablets designed to increase gastric retention times, buccal patches, and sublingual tablets.

The compounds may also be administered intravenously or intraperitoneally by infusion or injection. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds disclosed for use in the methods herein can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

In some embodiments, the pharmaceutical compositions described herein contain a therapeutically effective dose of the compound. The term "effective amount" or "therapeutically effective amount," as used herein, refers to the amount of the active compound that is effective to achieve its intended purpose after a single dose, wherein a single dose comprises one or more dosage units, or after a course of doses, e.g., during or at the end of the treatment period. The therapeutically effective amount will vary depending on the needs of the subject, but this amount can readily be determined by one of skill in the art, for example, a physician.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The compounds are conveniently administered in unit dosage form; for example, containing 0.05 to 10000 mg, 0.5 to 10000 mg, 5 to 1000 mg, or about 100 mg of active ingredient per unit dosage form. In some embodiments, the dosage unit contains about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 750 mg, or about 1000 mg of active ingredient.

The compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

Example 1

Murine Model Testing

Materials and Methods
Reagents.

Zileuton (5-lipoxygenase inhibitor), MK886 (inhibitor of 5-lipoxygenase-activating protein), and MK571, zafirlukast, montelukast, and pranlukast (cysteinyl leukotrienes type 1 receptor antagonists) (3, 6, 13, 21-23) were purchased from Cayman Chemical Company (Ann Arbor, Mich.). CP105696 (LTB4 receptor antagonist) was a gift from Pfizer.

Bacterial Strains.

E. coli K1 strain RS218 (O18:K1:H7) is a cerebrospinal fluid isolate from a neonate with meningitis (9, 10, 14, 28). E. coli K-12 strain HB101 was used as a non-invasive negative control. Bacteria were grown in brain heart infusion (BHI) broth containing appropriate antibiotics (Difco Liboratories, Detroit, Mich.).

Mouse Model of Experimental Hematogenous Meningitis.

Female 5-LO-/- (129-Alox5$^{tm1Fun/J}$) and strain-matched (129SvEv) wild-type mice, 9~12 week old and 18~26 gm, were used (23). Our pilot experiments revealed that intravenous administration of $1\times10^6$ colony forming units (CFUs) of E. coli K1 strain RS218 to wild type 129SvEv mice resulted in bacteremia of less than $10^3$ CFU/ml of blood at one hour and E. coli penetration into the brain was not observed, while intravenous administration of $1\times10^7$ CFUs resulted in bacteremia of greater than $10^3$ CFU/ml of blood at one hour and E. coli penetration into the brain occurred in all infected animals. Most animals receiving $1\times10^7$ CFUs, however, died between one and two hour of intravenous inoculation. Based on these observations, we examined and compared E. coli K1 penetration into the brain at one hour following intravenous administration of $1\times10^7$ CFUs of strain RS218 in 5-LO-/- and wild type mice.

Mice were anesthetized with pentobarbital sodium given subcutaneously at 50 mg/kg and each mouse received $1\times10^7$ CFU of E. coli RS218 in 100 μl PBS via the tail vein. One hour later, mouse chest was cut open, and blood from right ventricle was collected and plated for bacterial counts (CFUs). The mouse was, then, perfused with a mammalian Ringer's solution by transcardiac perfusion through a 23-gauge needle inserted into the left ventricle of the heart under the perfusion pressure of about 100 mmHg. The perfusate exited through a cut in the right atrium. The composition of the mammalian Ringer solution was: (in mM) 132 NaCl, 4.6 KCl, 2 $CaCl_2$, 1.2 $MgSO_4$, 5.5 glucose, 5.0 $NaHCO_3$, and 20 HEPES and Na-HEPES, containing 10 mg/ml BSA; pH of the Ringer solution was maintained at 7.40-7.45 by adjustment of the ratio of Na-HEPES to HEPES. Ringer solution used in this study has been shown not to affect the microvessel permeability (29). 30 min after perfusion of Ringer solution, mice were decapitated. The brains were removed, weighed and homogenized in 2 ml RPMI, followed by culturing for bacterial counts on LB agar plates containing streptomycin (50 μg/ml). Bacterial penetration into the brain was also expressed as (brain CFUs per gm/blood CFUs per ml)×100. Kidneys and spleens were also dissected out for determinations of bacterial counts (CFUs/gm).

Infant Rat Model of Experimental Hematogenous Meningitis.

Experimental hematogenous E. coli meningitis was induced in 5-day old rats as previously described (9, 10, 14, 28). Briefly, outbred, specific-pathogen-free pregnant Sprague-Dawley rats with timed conception were purchased from Charles River Breeding laboratory (Wilmington, Mass.). The rats delivered in our vivarium 5 to 7 days after arrival. At 5 days of age, all members of each litter were randomly divided into two groups, to receive intraperitoneally montelukast (50 μg/10 gm of weight in 50 μl PBS) or vehicle control (3.3% DMSO in 50 μl PBS). One hour later, each animal received $1\times10^7$ CFU of E. coli K1 strain RS218 via intracardiac injection. At one hour after bacterial injection, blood and CSF specimens were obtained as described previously (9, 10, 14, 28) for quantitative cultures. The development of E. coli meningitis (defined as positive CSF cultures) was compared between the two groups of animals.

Isolation, Characterization and Culture of Human Brain Microvascular Endothelial Cells (HBMEC).

HBMECs were isolated and characterized as described previously (26). Briefly, brain specimens were cut into small pieces and homogenized in DMEM containing 2% FBS (DMEM-S) using a Dounce homogenizer with a loose fitting. The homogenate was centrifuged in 15% dextran in DMEM-S for 10 min at 10 000 g. The pellet containing crude microvessels was further digested in a solution containing 1 mg/ml collagenase/dispase in DMEM-S for 1 h at 37° C. Microvascular capillaries were isolated by adsorption to a column of glass beads (0.25-0.3 mm), washing off the beads, and recovered in growth medium. HBMECs were plated on rat tail collagen/fibronectin-coated dishes or glass coverslips and cultured in RPMI 1640-based medium with growth factors, 10% heat-inactivated FBS, 10% NuSerum, 5 U heparin/ml, 2 mM L-glutamine, 1 mM sodium pyruvate, non-essential amino acids, vitamins and 100 U penicillin and streptomycin/ml. Viability of HBMEC was assessed by examining morphology and by trypan blue exclusion. HBMECs were positive for factor VIII-Rag, took up fluorescently labeled acetylated low-density lipoprotein and expressed γ-glutamyl transpeptidase. HBMECs were maintained in RPMI-based medium, including 10% FBS and 10% NuSerum (BD Biosciences), at 37° C. in a humid atmosphere of 5% CO2 as described previously (26).

E. coli Binding and Invasion Assays in HBMEC.

E. coli strain RS218 was grown overnight in BHI broth in the presence of streptomycin (50 μg/ml). Bacteria were resuspended in experimental medium [M199-HamF12 (1:1) containing 5% heat-inactivated fetal bovine serum, 2 mM glutamine, and 1 mM pyruvate] and added in a multiplicity of infection (MOI) of 100:1 to HBMEC grown in collagen-coated 24-well plates at 37° C. in 5% CO2 incubator for 90 min for binding assay as described previously (9, 10, 14, 28). HBMEC were washed four times with PBS to remove unbound bacteria, lysed in 0.025% Triton X-100 and plated for determinations of CFUs. The results were calculated as a percent of the initial inoculum and expressed as percent relative binding compared to percent binding of RS218 in the presence of vehicle control (DMSO). Each set was run in triplicates.

The HBMEC invasion assay with gentamicin treatment was performed to determine the number of viable intracellular bacteria recovered from the infected HBMEC, as previously described (9, 10, 14, 28). *E. coli* K1 strain RS218 was added to HBMEC as described above for binding assay. HBMEC were subsequently washed with RPMI 1640 and incubated with experimental media containing gentamicin (100 μg/ml) for 1 h to kill extracellular bacteria. The cells were washed again with PBS and lysed in 0.025% Triton X-100. The released intracellular bacteria were enumerated by plating on sheep blood agar plates. The results were calculated as a percent of the initial inoculum and expressed as percent relative invasion compared to percent invasion of RS218 in the presence of vehicle control (DMSO). Each set was run in triplicates.

To examine the effects of inhibitors and antagonists on *E. coli* K1 binding to and invasion of HBMEC, HBMEC were pretreated with inhibitors or antagonists for 30 mins before addition of *E. coli*, and then processed for binding and invasion assays as described above.

Statistical Analysis.

Data are expressed as mean±SEM. Differences of bacterial counts in the blood, brain, kidney, spleen, and percent of brain CFUs/blood CFUs between different groups of mice were determined by Wilcoxon rank sum test. Differences in bacterial counts from the brains between the two groups of infant rats were determined by Student's t test. Differences in the development of meningitis (defined as positive CSF cultures) were determined by the Fisher's exact test. Differences in bacterial binding to and invasion of HBMEC between assays with and without inhibitors/antagonists were determined by Student's t test. $P<0.05$ was considered significant.

Results

Previous experiments with transmission and scanning electron microscopy demonstrate that *E. coli* K1 internalization of HBMEC was associated with microvilli-like protrusions at the entry site on the surface of HBMEC and there was no evidence of membrane ruffling (15-17). In addition, *E. coli* invasion of HBMEC was inhibited by pretreatment of HBMEC with microfilament-disrupting agents such as cytochalasin D and latrunculin A (ref). These findings indicate that *E. coli* invasion of HBMEC involves the host cell actin cytoskeleton rearrangements, but the underlying mechanisms remain incompletely understood. We have previously shown that cPLA2α contributes to *E. coli* K1 invasion of HBMEC (4). Activation of PLA2 and arachidonic acid metabolites, prostaglandins and LTs have been linked with host cell actin cytoskeleton rearrangements (11). LTs comprise one major group of biologically potent lipid mediators and are synthesized from arachidonate by 5-lipoxygenase (5-LO).

We examined whether 5-LO contributes to *E. coli* penetration into the brain by studying 5-LO−/− mice as compared to their strain-matched wild type 129/SvEv mice. Each animal received $1\times10^7$ colony forming units (CFUs) of *E. coli* K1 strain RS218 via the tail vein. One hour later, the blood specimens were obtained for determination of CFUs. The animals were then perfused with sterile Ringer's solution until the perfused solution became colorless. The brains as well as the spleens and the kidneys were removed, weighed, homogenized and cultured for determinations of CFUs. The magnitude of bacteremia, as determined by bacterial counts in the blood (CFU/ml), did not differ significantly between the two groups of 5-LO−/− and wild type animals (see FIG. 1A), but the bacterial counts recovered from the brains were significantly less in 5-LO−/− mice than in their wild type animals (see FIG. 1C). These findings indicate that significantly decreased penetration of *E. coli* K1 into the brain of 5-LO−/− mice was not the result of lower levels of bacteremia in 5-LO−/− mice compared to their wild type mice. This is also shown by the percent of bacterial counts in the brain compared to those in the blood, which was significantly less in 5-LO−/− mice than in their wild type animals (see FIG. 1D). The bacterial counts in the spleens and kidneys (CFUs/gm), however, did not differ between the two groups of animals (see FIG. 1B).

The enzyme 5-LO, in conjunction with 5-LO-activating protein (FLAP), oxygenates arachidonic acid to leukotriene A4 (LTA4). This unstable intermediate can be hydrolyzed to form the LTB4 or conjugated with glutathione to form the cysteinyl leukotrienes (LTC4, LTD4 and LTE4) (22, 23).

Since *E. coli* K1 invasion of HBMEC in vitro is a prerequisite for penetration into the brain in vivo (15-17), our next experiments examined the effects of 5-LO and FLAP inhibitors (zileuton and MK886, respectively) in *E. coli* K1 invasion of HBMEC. Pretreatment of HBMEC with zileuton and MK886 significantly inhibited *E. coli* K1 invasion of HBMEC in a dose-dependent manner (FIG. 2A). These in vitro findings, together with the in vivo findings of significantly decreased *E. coli* penetration into the brain of 5-LO−/− mice, indicate that endogenous LT biosynthesis via 5-LO and FLAP plays an important role in *E. coli* K1 invasion of HBMEC and penetration into the brain.

The biological actions of LTB4 and cysteinyl LTs are transduced by ligation of specific G-protein coupled receptors (GPCRs), which initiate activation of specific intracellular signaling cascades. The leukotriene GPCRs for LTB4 have been designated BLT-1 and BLT-2, while those recognizing cysteinyl LTs are designated CysLT1 and CysLT2 (22, 23). We next examined which class of LTs is involved in *E. coli* K1 invasion of HBMEC using CysLT1 antagonists (MK571, zafirlukast, montelukast and pranlukast) and BLT1 antagonist (CP105696). As shown in FIG. 2B, all four CysLT1 antagonists were effective in inhibiting *E. coli* invasion of HBMEC in a dose-dependent manner, while CP105696 (BLT1 antagonist) failed to exhibit any inhibition of *E. coli* invasion of HBMEC.

We next examined one of the CysLT1 antagonists (MK571) for its effect on *E. coli* K1 penetration into the brain. As shown in FIGS. 1C and D, MK571 significantly decreased *E. coli* K1 penetration into the brain of wild type mice to the level observed in 5-LO−/− mice, but did not affect the bacterial counts in the blood, spleens and kidneys compared to the vehicle control (see FIG. 1A,B). These in vitro and in vivo findings demonstrate for the first time that cysteinyl LTs contribute to *E. coli* K1 invasion of HBMEC and penetration into the brain.

We also examined one of the CysLT1 antagonists for its effect on *E. coli* K1 penetration into the brain in our well-characterized infant rat model of experimental hematogenous *E. coli* meningitis (9, 10, 14, 28). At 5 days of age, all members of each litter were randomly divided to receive intraperitoneally montelukast or vehicle control. One hour later, animals received $1\times10^7$ CFU of *E. coli* strain RS218 via intracardiac injection. At one hour after bacterial inoculation, blood and cerebrospinal fluid (CSF) specimens were obtained for quantitative cultures. Bacterial counts in the blood did not differ between the two groups of animals receiving montelukast or vehicle control (Table 1).

TABLE 1

Comparison of bacterial counts in the blood and development of meningitis (defined as positive CSF cultures) between two groups of 5-day-old rats receiving montelukast or vehicle control (3.3% DMSO)

| Inhibitor | No. of animals | Bacteremia (log CFU/ml of blood, mean ± SD) | No. (%) of animals with meningitis |
| --- | --- | --- | --- |
| Montelukast | 9 | 7.07 ± 0.26 | 2 (22%)* |
| DMSO | 9 | 6.97 ± 0.57 | 9 (100%) |

*$p < 0.001$ by Fisher's exact test

However, the development of *E. coli* meningitis (defined as positive CSF cultures) was significantly less in the recipients of montelukast compared to the vehicle control (Table 1). These findings indicate the involvement of cysteinyl LTs in *E. coli* K1 penetration into the brain, and also demonstrate the first novel application of CysLT1 antagonists to prevention of lethal *E. coli* meningitis.

Discussion

*E. coli* K1 invasion of HBMEC is a prerequisite for penetration into the brain (9, 10, 14, 28). Our previous studies have shown that *E. coli* K1 penetration into the brain requires a high-degree of bacteremia as well as *E. coli* interaction with HBMEC, involving specific host cell signaling molecules including cPLA2α.

We have shown herein that cPLA2α contributes to *E. coli* K1 invasion of HBMEC (4). The role of cPLA2α in mediating agonist-induced arachidonic acid release for eiconsanoid production such as leukotrienes (LTs) is well established (8, 22, 23). LTs are synthesized from arachidonate by 5-LO and specific GPCRs recognize LTB4 and cysteinyl LTs. We showed for the first time that 5-LO and cysteinyl LTs are involved in *E. coli* K1 invasion of HBMEC and penetration into the brain.

We showed that inhibitors of 5-LO and FLAP and CysLT1 antagonists exhibited a does-dependent inhibition of *E. coli* K1 invasion of HBMEC, while the BLT-1 antagonist failed to exhibit any inhibition of *E. coli* invasion of HBMEC.

More importantly, however, the CysLT1 antagonists were effective in inhibition of *E. coli* K1 penetration into the brain in two different models of experimental hematogenous *E. coli* meningitis. In the mouse model, intravenous administration of $1 \times 10^7$ CFUs of *E. coli* K1 strain RS218 to wild type 129SvEv mice resulted in bacteremia of greater than $10^3$ CFU/ml of blood, while intravenous administration of $1 \times 10^6$ CFUs resulted in bacteremia of less than $10^3$ CFU/ml of blood at one hour. *E. coli* penetration into the brain occurred in all infected animals who developed bacteremia of greater than $10^3$ CFU/ml of blood, while *E. coli* penetration into the brain was not observed in animals developing bacteremia of less than $10^3$ CFU/ml of blood. A previous study in humans also points to a relationship between the magnitude of bacteremia and the development of *E. coli* meningitis (5). For example, a significantly higher incidence of *E. coli* meningitis was observed in neonates who had bacterial counts in blood higher than $10^3$ CFU/ml, compared to those with bacterial counts in blood lower than $10^3$ CFU/ml. These findings support the concept that a magnitude of bacteremia is an important determinant for *E. coli* penetration into the brain. In the mouse model, the magnitudes of bacteremia were similar between wild type mice and 5-LO−/− mice or wild type mice receiving the CysLT-1 antagonist (MK571). Therefore, the significantly decreased penetrations of *E. coli* K1 into the brains of 5-LO−/− mice and wild type mice receiving the CysLT-1 antagonist (MK571) compared to wild type mice are not the results of decreased levels of bacteremia. Similarly, in our well characterized infant rat model of experimental hematogenous meningitis, the CysLT-1 antagonist (montelukast) was effective in significantly decreasing the prevalence of meningitis (defined as positive CSF culture) compare to the vehicle control, despite having similar levels of bacteremia. Taken together, these in vitro and in vivo findings demonstrate that cysteinyl LTs contribute to *E. coli* traversal of the blood-brain barrier and penetration into the brain, and studies are needed to elucidate the underlying mechanisms.

LTs are shown to have pathophysiological roles in respiratory diseases, allergic diseases and cardiovascular diseases (6, 7, 21, 23). Our findings reported here demonstrate for the first time that CysLTs contribute to *E. coli* traversal of the blood-brain barrier, an essential step required for development of *E. coli* meningitis. Increasing resistance to antimicrobial agents, including extended-spectrum beta-lactamase-producing *E. coli* is an important factor contributing to high mortality and morbidity associated with *E. coli* meningitis. Our findings illustrate that targeting host cell signaling molecules involved in microbial traversal of the blood-brain barrier, as shown here with the CysLT-1 antagonists, limits the exposure to emerging antimicrobial resistant bacteria and provides an innovative concept and approach to prevention of *E. coli* meningitis. Of particular relevance to this approach is the availability of inhibitors of 5-LO and FLAP as well as CysLT1 antagonists, which have been developed for asthma and shown to be safe and well tolerated in clinical trials in asthma (3, 6, 13, 21-23).

Example 2

Materials and Methods

Reagents.

Arachidonic acid (AA) was purchased from Cayman Chemical Company (Ann Arbor, Mich.). Evans blue dye was purchased from Sigma (St Louis, Mo.). Arachidonyl trifluoromethylketone (AACOCF3; cPLA2 inhibitor) was purchased from Biomol Laboratories. (Plymouth Meeting, Pa.)

Mice cPLA2α−/− and wild type mice, either male or female, 1013 week old that had been backcrossed on the BALB/c strain for >10 generations were used[14]. All procedures and handling techniques were approved by The Johns Hopkins Animal Care and Use Committee.

Isolation, Characterization and Culture of Human or Mouse BMEC.

Human or mouse BMECs were isolated and characterized as described previously[13,15]. Briefly, brain specimens were cut into small pieces and homogenized in DMEM containing 2% FBS (DMEM-S) using a Dounce homogenizer with a loose fitting. The homogenate was centrifuged in 15% dextran in DMEM-S for 10 min at 10 000 g. The pellet containing crude microvessels was further digested in a solution containing 1 mg/ml collagenase/dispase in DMEM-S for 1 h at 37° C. Microvascular capillaries were isolated by adsorption to a column of glass beads (0.25-0.3 mm) and washing off the beads. BMECs were plated on rat tail collagen/fibronectin-coated dishes or glass coverslips and cultured in RPMI 1640-based medium with growth factors, 10% heat-inactivated FBS, 10% NuSerum, 5 U heparin ml-1, 2 mM L-glutamine, 1 mM sodium pyruvate, non-essential amino acids, vitamins and 100 U penicillin and streptomycin ml-1-1. BMECs were positive for factor VIII-Rag, took up fluorescently labeled acetylated low-density lipoprotein and expressed γ-glutamyl transpeptidase. BMECs were maintained in RPMI-based medium, including 10% FBS and 10% NuSerum (BD Biosciences), at 37° C. in a humid atmosphere of 5% CO2 as described previouslyl[13,15].

E. coli Binding and Invasion Assays in BMECs

E. coli strain RS218 (O18:K1:H7), a cerebrospinal fluid isolate from a neonate with meningitis, was grown overnight in brain heart infusion (BHI) broth (Difco Laboratories, Detroit, Mich.). Bacteria were resuspended in experimental medium [M199-HamF12 (1:1) containing 5% heat-inactivated fetal bovine serum, 2 mM glutamine, and 1 mM pyruvate] and added in a multiplicity of infection (MOI) of 100:1 to BMECs grown in collagen-coated 24-well plates at 37° C. in 5% $CO_2$ incubator for 90 min for binding assay, as previously described[11]. BMECs were washed four times with PBS to remove unbound bacteria, lysed in 0.025% Triton X-100 and plated for determinations of CFUs. The results were calculated as a percent of the initial inoculum and expressed as percent relative binding compared to percent binding of RS218 in the presence of vehicle control (DMSO). Each set was run in triplicates.

The BMEC invasion assay with gentamicin treatment[11] was performed to determine the number of viable intracellular bacteria recovered from the infected BMECs. E. coli K1 strain RS218 was added to BMEC as described above for binding assay. BMECs were subsequently washed with RPMI 1640 and incubated with experimental media containing gentamicin (100 μg/ml) for 1 h to kill extracellular bacteria. The cells were washed again with PBS, lysed in 0.025% Triton X-100, and the released intracellular bacteria were enumerated by plating on sheep blood agar plates. The results were calculated as a percent of the initial inoculum and expressed as percent relative invasion compared to percent invasion of RS218 in the presence of vehicle control (DMSO). Each set was run in triplicates.

Mouse Model of Experimental Hematogenous Meningitis

Each mouse received $1\times10^7$ CFU of E. coli K1 strain RS218 in 100 μl PBS via the tail vein. One hour later, mouse chest was cut open, and blood from right ventricle was collected and plated for bacteria counts, which were expressed as CFUs/ml of blood. The mouse was then perfused with a mammalian Ringer's solution by transcardiac perfusion through a 23-gauge needle inserted into the left ventricle of the heart under the perfusion pressure of about 100 mmHg. The perfusate exited through a cut in the right atrium. The composition of the mammalian Ringer solution was: (in mM) 132 NaCl, 4.6 KCl, 2 $CaCl_2$, 1.2 $MgSO_4$, 5.5 glucose, 5.0 $NaHCO_3$, and 20 HEPES and Na-HEPES, containing 10 mg/ml BSA; pH of the Ringer solution was maintained at 7.40-7.45 by adjustment of the ratio of Na-HEPES to HEPES. Our pilot experiments revealed that no bacteria were recovered from the blood after 30 min perfusion with Ringer solution, and bacterial counts recovered from the brain were, therefore, most likely to represent the E. coli that had penetrated into the brain. The brains were removed, weighed and homogenized in 2 ml RPMI followed by plating for bacterial counts, which were expressed as CFUs/gm. Since E. coli K1 penetration into the brain is shown to depend on the magnitude of bacteremia[5,7], bacterial penetration into the brain was also expressed as [(brain CFUs per gm)/(blood CFUs per ml)]×100. Kidneys and spleens were also removed, homogenized and plated for determination of bacterial counts, which were expressed as CFUs/gm.

Blood-Brain Barrier (BBB) Permeability

Integrity of BBB was assessed by measuring extravasation of intravenously administered Evans blue dye into the brain. 2% Evans blue in 100 μl PBS solution was injected through the tail vein 10 min after injection of E. coli RS218. 50 min later, mice were perfused with Ringer's solution (details see the method "Mouse model of experimental hematogenous meningitis"). After measurement of protein concentration, 0.5 ml of 60% trichloroacetic acid (Sigma) was added to 0.5 ml brain homogenates and mixed well on a vortex for 2 min to precipitate protein. The samples were placed on ice for 30 min and centrifuged for 30 min at 1000×g. Evans blue concentration in the supernatants was measured at 610 nm and calculated according to a standard curve[16]. Evans blue extravasation was expressed as μg/mg of brain protein[17].

Statistical Analysis.

Data are expressed as mean±SEM. Differences of bacterial counts in the blood, brain, kidney, spleen, and percent of brain CFUs/blood CFUs between different experimental groups were determined by Wilcoxon rank sum test. Differences in bacterial binding and invasion of BMECs between assays with and without inhibitors were determined by one-way ANOVA followed by Dunnett's test. The level of significance was set at P<0.05.

Results

Role of cPLA2α in E. coli invasion of BMECs.

Our first experiment was to examine the effect of a pharmacological inhibitor of cPLA2α (arachidonyl trifluoromethylketone or AACOCF3) on the interaction of E. coli K1 strain RS218 with human and mouse BMECs. We have previously shown that AACOCF3 exhibited a dose-dependent inhibition of E. coli K1 invasion of human BMECs, and human BMECs were used as a control[13]. Strain RS218 is the cerebrospinal fluid isolate from a neonate with E. coli meningitis and represents the most common prototypic strain for meningitis-causing E. coli[5]. Treatment with AACOCF3 inhibited E. coli invasion of both human and mouse BMECs in a dose-dependent manner, whereas AACOCF3 did not affect the binding of E. coli to BMECs (see FIG. 3). These findings suggest that cPLA2α is likely to play a role in E. coli invasion of BMECs.

Role of cPLA2α in E. coli Penetration into the Brain.

We have shown that E. coli K1 invasion of BMECs is a pre-requisite for penetration into the CNS[1-3]. Since cPLA2α inhibitor was efficient in inhibiting E. coli K1 invasion of mouse BMECs, we next examined its role using gene deletion and pharmacological inhibition the role of cPLA2α in E. coli K1 penetration into the brain in the mouse model of experimental hematogenous meningitis.

We examined and compared the ability of E. coli K1 to penetrate into the brain between cPLA2α−/− and their wild type BALB/c mice. Each animal received $1\times10^7$ CFUs of E. coli K1 strain RS218 via the tail vein. One hour later, the blood specimens were obtained for determination of CFUs, and the animals perfused with sterile Ringer's solution until the perfused solution became colorless. The brains as well as the spleens and the kidneys were removed, weighed, homogenized and plated for determinations of CFUs. The magnitude of bacteremia did not differ significantly between the two groups of cPLA2α−/− and wild type animals, as shown by similar bacterial counts in the blood (CFU/ml) (FIG. 4a), but the bacterial counts in the brains were significantly less in cPLA2α−/− mice than in their wild type animals (FIG. 4c). These findings indicate that significantly decreased penetration of E. coli K1 into the brain of cPLA2α−/− mice was not the result of lower levels of bacteremia in cPLA2α−/− mice compared to their wild type mice. This is also shown by the percent of bacterial counts in the brain compared to those in the blood, which was significantly less in cPLA2α-/- mice than in their wild type animals (see FIG. 4d). Of interest, the bacterial counts in the spleens and kidneys (CFUs/gm) did not differ between the two groups of animals (FIG. 4b).

We next examined whether inhibition of cPLA2α with AACOCF3 affects E. coli K1 penetration into the brain of the wild type mice. Intravenous administration of AACOCF3 (4 mM in 50 μl PBS) 30 mins before bacterial injection significantly decreased the brain penetration of E. coli K1 in the wild type mice to the level observed in cPLA2α-/- mice (FIGS. 4c and 4d). This dose of AACOCF3 was shown to inhibit cPLA2 activity in mice[10]. In contrast, AACOCF3 did not affect the bacterial counts in the blood, spleens and kidneys compared to the vehicle control (FIGS. 4a and 4b). These in vitro and in vivo findings demonstrate that cPLA2α contributes to the penetration of E. coli K1 into the brain, but not into non-brain organs.

Effect of Arachidonic Acid in E. Coli K1 Penetration into the Brain.

cPLA2α selectively liberates arachidonic acid from the sn-2 position of membrane phospholipids[18,19]. We next examined whether exogenous arachidonic acid affects E. coli K1 penetration into the brain of cPLA2α-/- mice. Intravenous administration of arachidonic acid (1.2 μg/mouse in 50 μl PBS) 30 mins before bacterial injection did not affect the bacterial counts in the blood, spleens and kidneys (FIGS. 4a and 4b), but significantly enhanced E. coli K1 penetration into the brain to the level observed in the wild type mice (FIGS. 4c and 4d). This dose of arachidonic acid was shown to restore cPLA2α-dependent vascular responses in cPLA2α-/- mic[20].

Figure 5:
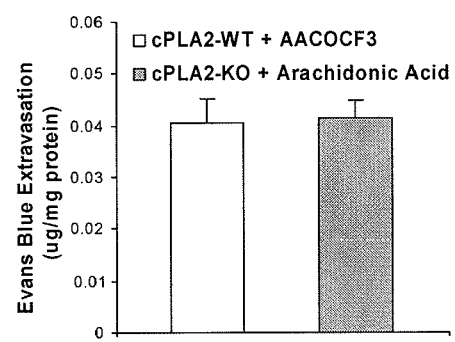
FIG. 5 shows AACOCF3 or arachidonic acid did not affect the blood-brain barrier permeability. Evans blue dye extravasation into the brain tissue was used as an indicator of the blood-brain barrier permeability in cPLA2α-/- (KO) and wild type (WT) mice. 4 mM AACOCF3 in 50 µl PBS, or 1.2 µg arachidonic acid in 100 µl PBS was injected through the tail vein 30 min before bacterial injection. At 10 min after bacteria injection, 2% Evans blue in 100 µl PBS was injected through the tail vein, and 50 min later, mice were perfused with Ringer's solution for 30 min followed by removal of the brain for subsequent Evans blue measurements. Data shown are mean±SEM. WT+AACOCF3 (n=3), KO+ arachidonic acid (n=3).

The enhancement of E. coli K1 penetration into the brain by arachidonic acid in cPLA2α-/- mice was not accompanied by any changes in the blood-brain barrier permeability, as shown by no significantly increased extravasation of intravenously administered Evans blue dye into the brain compared to the wild type mice receiving AACOCF3 (FIG. 5). These findings are consistent with those of our previous studies, where we showed that E. coli K1 traversal of the blood-brain barrier was not associated with any changes in the integrity of the blood-brain barrier[8].

Discussion

Deletion of a functional cPLA2α has been shown to attenuate the development of arthritis, bone resorption and pulmonary fibrosis[21-23]. The findings reported here demonstrate for the first time the novel role of cPLA2α in E. coli K1 penetration into the brain, an essential step required for the development of meningitis.

In the mouse model, intravenous administration of 1×10$^7$ CFUs of E. coli K1 strain RS218 to wild type 129SvEv mice resulted in bacteremia of greater than 10$^3$ CFU/ml of blood, while intravenous administration of 1×10$^6$ CFUs resulted in bacteremia of less than 10$^3$ CFU/ml of blood at one hour. E. coli penetration into the brain was found to occur in all infected mice developing bacteremia of greater than 10$^3$ CFU/ml of blood, while E. coli penetration into the brain was not observed in animals developing bacteremia of less than 10$^3$ CFU/ml of blood. A previous study in humans also points to a relationship between the magnitude of bacteremia and the development of E. coli meningitis[21]. For example, a significantly higher incidence of E. coli meningitis was observed in neonates who had bacterial counts in blood higher than 10$^3$ CFU/ml, compared to those with bacterial counts in blood lower than 10$^3$ CFU/ml. These findings show that a magnitude of bacteremia is an important determinant for E. coli penetration into the brain in both humans and experimental animals.

We showed that E. coli K1 penetrations into the brains of cPLA2α-/- mice and wild type mice receiving the cPLA2α inhibitor (AACOCF3) were significantly less compared to wild type mice, but the magnitudes of bacteremia were similar among cPLA2α-/- mice, wild type mice, and wild type mice receiving the cPLA2α inhibitor. Therefore, the significantly decreased penetration of E. coli K1 into the brains of cPLA2α-/- mice and wild type mice receiving the cPLA2α inhibitor (AACOCF3) was not the result of decreased levels of bacteremia. cPLA2α, however, did not affect E. coli K1 penetration into the non-brain organs such as kidneys and spleens. We have previously shown that E. coli K1 invasion of endothelial cells occurs in human BMEC, but not in non-brain endothelial cells such as human umbilical endothelial cells, human aortic arterial endothelial cells and human iliac vein endothelial cells[24].

Increasing resistance to antimicrobial agents including extended-spectrum β-lactamase-producing E. coli is an important contributing factor to high mortality and morbidity associated with E. coli meningitis[25,26]. Our findings demonstrate that targeting specific host cell signal transduction pathways involved in microbial traversal of the blood-brain barrier, as shown here with cPLA2α, limits the exposure to emerging antimicrobial resistant bacteria and provides an innovative concept to prevention of E. coli meningitis.

Example 3

C. neoformans Additional Studies

Cryptococcus neoformans (C. neoformans) is an encapsulated yeast responsible for common opportunistic life-threatening meningitis/meningoencephalitis, mainly in patients infected with HIV-1. C. neoformans is the common cause of culture-positive meningitis in areas of the world where HIV is endemic (e.g., Zimbabwe, Malawi, and Cambodia). C. neoformans meningitis/meningoencephalitis is well documented for its high mortality and morbidity. C. neoformans is commonly acquired by inhalation, and extrapulmonary dissemination can lead to infection of the bloodstream and subsequent dissemination to target organs, most commonly resulting in meningitis/meningoencephalitis. Several lines of evidence indicate that C. neoformans penetration into the brain follows fungemia, and cerebral capillaries are the portal of entry into the brain. We have developed the in vitro blood-brain barrier model by isolation and cultivation of human brain microvascular endothelial cells (HBMEC). Upon cultivation on collagen-coated Transwell inserts the HBMEC monolayers exhibit morphological and functional properties of tight junction formation and polar monolayer. Our studies revealed that C. neoformans traversal of the HBMEC monolayers occurs without affecting the HBMEC integrity.

Figure 2:
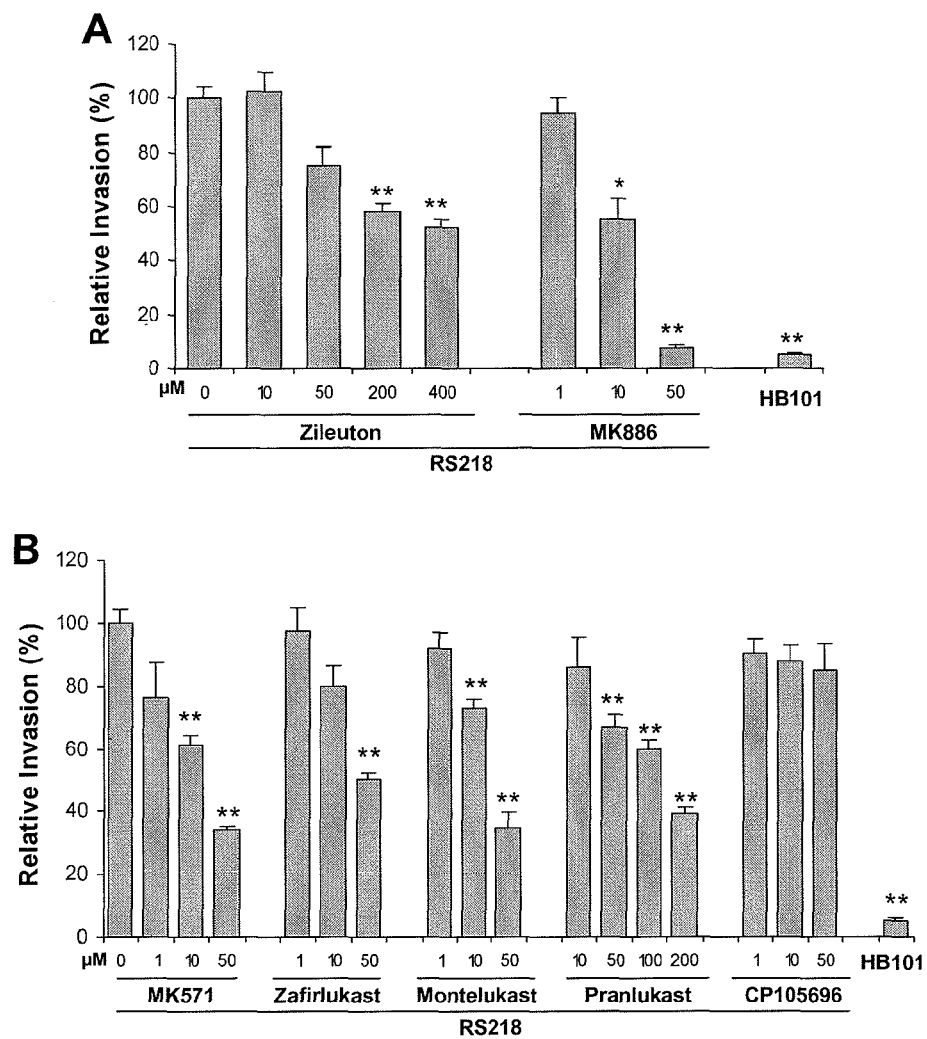
FIG. 2 shows *E. coli* K1 invasion of HBMECs was dose-dependently inhibited by 5-LO and FLAP inhibitors (zileuton and MK886, respectively) as well as by CysLT1 antagonists (MK571, zafirlukast, montelukast, and pranlukast), but not by BLT1 antagonist (CP105696). A laboratory *E. coli* K-12 strain HB101 was used as a negative control. Data shown are mean±SEM. Each experiment was performed in triplicate. *P<0.05; **P<0.01, Student's t-test, compared to vehicle control (DMSO).
Figure 3:
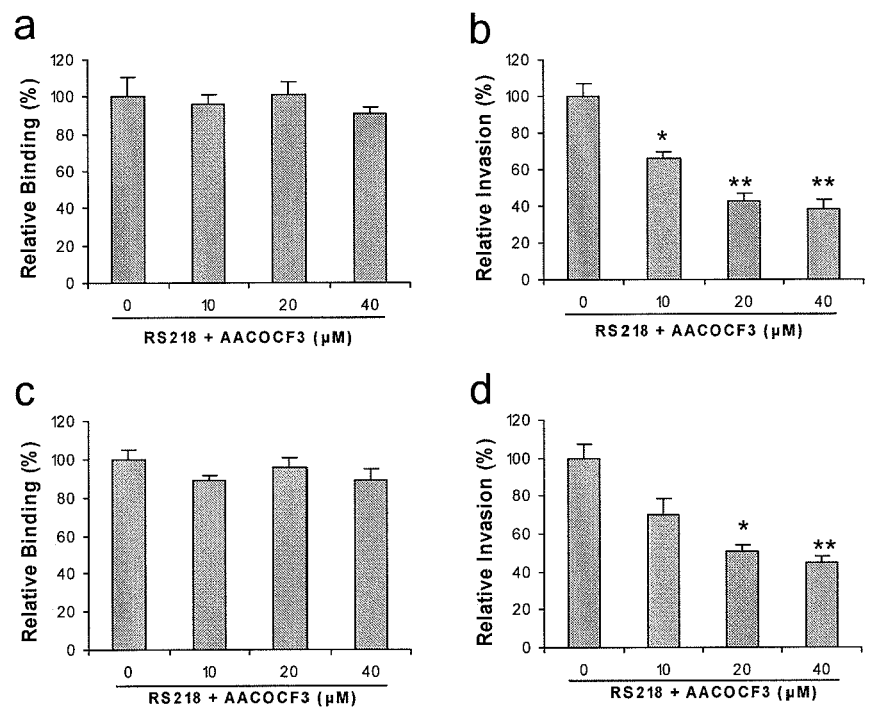
FIG. 3 shows AACOCF3 (a cPLA2α inhibitor) inhibited *E. coli* K1 invasion of BMECs in a dose-dependent manner, but it did not affect the binding of *E. coli* K1 to BMECs. Human BMECs (a, b) or mouse BMECs (c, d) were pretreated with AACOCF3 at indicated concentrations (10, 20, and 40 µM) for 60 min followed by bacterial binding and invasion assays. Data shown are mean±SEM. Each experiment was performed in triplicate. *P<0.05; **P<0.01, one-way ANOVA followed by Dunnett's test, compared to vehicle control (DMSO).
Figure 4:
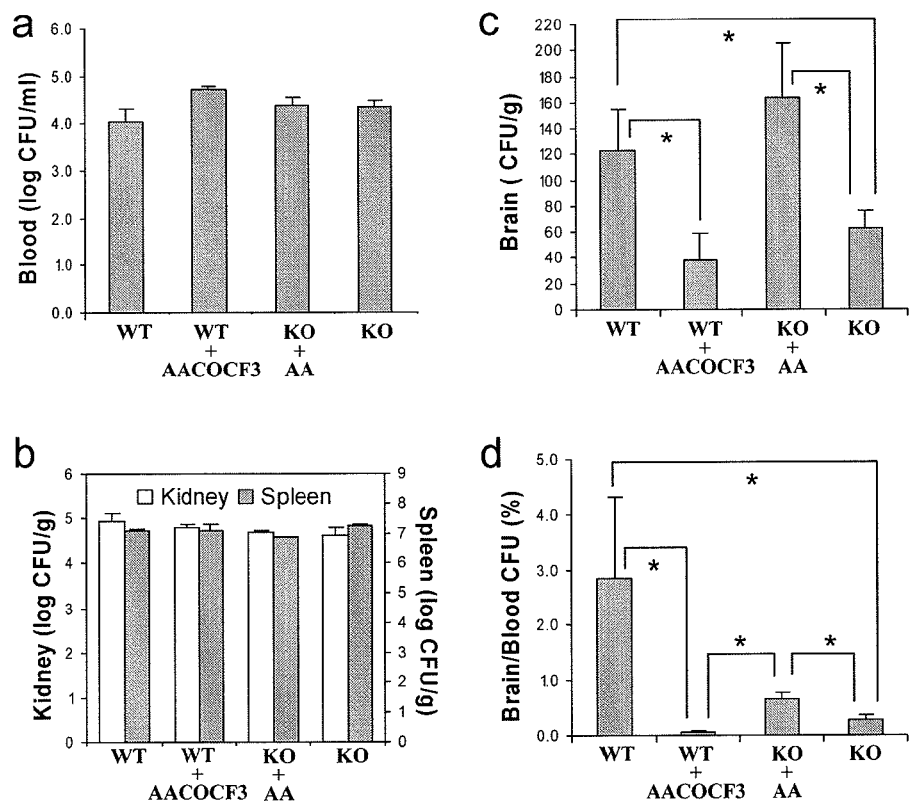
FIG. 4 shows *E. coli* K1 penetration into the brain was significantly less in cPLA2α-deficient mice (KO) compared to their wild type mice (WT). AACOCF3 significantly inhibited *E. coli* penetration into the brains of wild type mice, and arachidonic acid (AA) rescued the decreased *E. coli* penetration into the brains of cPLA2α-/- mice to the level in the wild type brains. Bacterial counts in the blood (CFU/ml) (a), kidneys and spleens (CFU/gm) (b), brains (CFU/gm) (c), and the percent of brain CFU per gm/blood CFU per ml (d) were determined one hour after intravenous injection of *E. coli* K1 strain RS218. To study the effect of cPLA2α inhibitor on *E. coli* penetration into the brain, 4 mM AACOCF3 in 50 µl PBS were injected through the tail vein of wild type mice 30 min before bacterial injection. Rescue experiments were performed with injection of 1.2 µg arachidonic acid (AA) in 100 µl PBS through the tail vein of cPLA2α-/- mice 30 min before bacterial injection. Data shown are mean±SEM. *P<0.05, Wilcoxon rank sum test, compared between WT (n=10), WT+AACOCF3 (n=3), KO+AA (n=3), and KO (n=12).

Several lines of evidence from experimental mouse models of C. neoformans meningitis/meningoencephalitis following intravenous inoculation as well as from cases of human C. neoformans meningitis/meningoencephalitis demonstrate that C. neoformans invasion into the brain follows fungemia, and cerebral capillaries, not the choroid plexus are the portal of entry into the brain (10-13, 21-23) (FIGS. 2, 3 and 4 of Studies).

The blood-brain barrier is a structural and functional barrier that is formed by brain microvascular endothelial cells (14, 24). It regulates the passage of molecules into and out of the brain to maintain the neural microenvironment. Brain microvascular endothelial cells possess distinct features such as tight junctions between them, and low rates of pinocytosis. The blood-brain barrier protects the brain from any microbes and toxins circulating in the blood. Recent studies, however, have shown that meningitis-causing microorganisms including C. neoformans can cross the blood-brain barrier as live organisms (11, 24).

We have isolated and cultivated HBMEC from children and adults (11, 14-17, 24-31). The resulting HBMEC were positive for factor VIII, carbonic anhydrase IV, Ulex Europaeus Agglutinin I, and took up acetylated low-density lipoprotein (AcLDL), and expressed gamma-glutamyl transpeptidase, demonstrating their brain endothelial cell characteristics. HBMEC were purified by fluorescent activated sorting (FACS) using 1,1'-dioctadecyl-1-3,3,3',3'-tetramethyl-indocarbocyanine perchlorate labeled-AcLDL (DiI-AcLDL) and found to be >99% pure endothelial cells based on specific marker studies. More importantly, upon cultivation on collagen-coated Transwell inserts these HBMEC exhibit morphologic and functional properties of tight junction formation as well as polar monolayer. These are shown by our demonstrations of tight junction proteins (such as ZO-1), and adherens junction proteins (such as β-catenin) and their spatial separation, limited transendothelial permeability to inulin (m.w. 4,000), and development of high transendothelial electrical resistance (11, 14-17).

Our experiments with transmission electron microscopy demonstrate that C. neoformans internalized into HBMEC. Microbial internalizations into non-professional phagocytic cells such as endothelial cells are shown to occur mainly via two different mechanisms involving the host cell actin cytoskeleton rearrangements, e.g., a zipper mechanism involving the formation of cell protrusions in contact with the pathogens and a trigger mechanism involving the formation of membrane ruffling around the pathogens (42, 43). C. neoformans internalization of HBMEC was associated with microvilli-like protrusions at the entry site on the surface of HBMEC.

There is considerable evidence that C. neoformans infection is able to modulate the host immune response through various fungal products, which include the capsular polysaccharide, mannitol, mating types, melanin, phenotyping switching, phospholipase, prostaglandins and urease (7-10, 15-19, 34-39), but their contributions to C. neoformans traversal of the blood-brain barrier remain incompletely understood.

Figure 11:
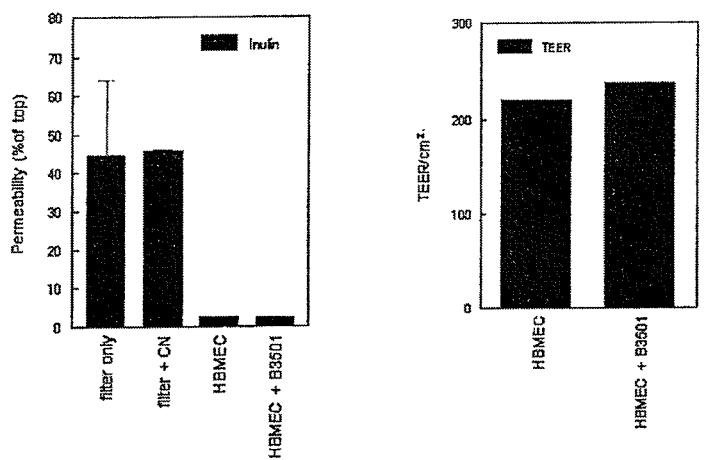
FIG. 11 shows the integrity of HBMEC monolayers did not change with traversal of *C. neoformans* (CN), as determined by (left) inulin permeability and (right) TEER.

Our studies using pharmacological inhibition and/or gene deletion revealed for the first time that host $cPLA_{2\alpha}$ is involved in C. neoformans traversal of the HBMEC monolayers and penetration into the brain. We showed that pharmacological inhibition of $cPLA_{2\alpha}$ was efficient in inhibiting C. neoformans traversal of the HBMEC monolayers. In addition, we showed that C. neoformans penetration into the brain was significantly less in $cPLA_{2\alpha}-/-$ mice compared to their strain-matched wild type mice, as shown by significantly decreased yeast counts (colony forming units or CFUs) recovered from the brains (CFU/gm) following intravenous inoculation in $cPLA_{2\alpha}-/-$ mice than in their wild type mice (FIG. 11 of Studies). These findings indicate that C. neoformans traverses HBMEC monolayers and penetrates into the brain by exploiting specific host cell molecules involving $cPLA_{2\alpha}$.

In mammalian cells, phospholipase A2 (PLA2) is involved in several pathophysiological conditions by producing precursors of inflammatory molecules from phospholipids such as leukotrienes (LTs) (11, 32). Previous studies have linked activation of PLA2 and arachidonic acid metabolites with host cell actin cytoskeleton rearrangements (33). There are six enzymes classified as group IV cPLA2, which include $cPLA_{2\alpha}$ (32). $cPLA_{2\alpha}$ has preferences for arachidonic acid as a substrate sn-2 fatty acyl moiety, and its role in mediating agonist-induced arachidonic acid release for eicosanoid production such as LTs is well established (11, 32, 49).

LTs comprise a group of biologically potent lipid mediators synthesized by 5-lipoxygenase (5-LO) from 20-carbon polyunsaturated fatty acid, predominantly arachidonate. The enzyme 5-LO, in conjunction with 5-LO-activating protein (FLAP), oxygenates arachidonic acid to LTA4. This unstable intermediate can be hydrolyzed to form the dihydroxyeicosatetraenoate LTB4 or conjugated with glutathione to form the cysteinyl LTs (LTC4, LTD4 and LTE4) (11). Both of these terminal leukotrienes (LTB4 and cysteinyl LTs) are biologically active in that specific G-protein coupled receptors (GPCRs) recognize these chemical structures and receptor recognition initiates complex intracellular signaling cascades. For example, the leukotriene GPCRs have been designated BLT-1 and BLT-2 that bind to LTB4 specifically, and CysLT1 and CysLT2 which are known to bind to the cysteinyl LTs (LTC4, LTD4 and LTE4) (11, 12).

Our next studies showed that the yeast counts recovered from the brains (CFU/gm) were significantly less in 5-LO-/- mice compared to their strain-matched wild type mice following intratracheal inoculation of C. neoformans. In addition, a CysLT1 antagonist (e.g., montelukast) exhibited a dose-dependent inhibition of C. neoformans traversal of the HBMEC monolayers and also significantly decreased the yeast counts recovered from the brains of wild type mice compared to the recipients of vehicle control.

Taken together, these findings suggest that 5-LO and cysteinyl LTs can be involved in C. neoformans traversal of the blood-brain barrier following intravenous and intratracheal inoculations.

Of relevance to this application is the availability of $cPLA_{2\alpha}-/-$, 5-LO-/- and CysLT1-/- mice as well as the availability of inhibitors of $cPLA_{2\alpha}$, 5-LO and FLAP, and CysLT1 receptor antagonists. Inhibitors of 5-LO and FLAP, and CysLT1 antagonists have been developed for asthma and shown to be safe and well tolerated in clinical trials, e.g., zileuton, montelukast, pranlukast and zafirlukast.

Our next studies showed that C. neoformans activates protein kinase C (PKC), but PKC activation in response to C. neoformans was decreased in the presence of $cPLA_{2\alpha}$ inhibitor. These findings suggest for the first time that the contributions of $cPLA_{2\alpha}$ and cysteinyl LTs to C. neoformans traversal of HBMEC monolayers are likely to involve PKC.

Additional Studies

A. Mouse Model of C. neoformans Meningitis/Meningoencephalitis Following Intravenous Inoculation.

Our in vitro and in vivo experiments used two C. neoformans strains that have been used for genome sequencing, B-3501A (serotype D) and H99 (serotype A). C. neoformans isolates of serotypes A or D mainly infect immunocompromised individuals. Serotype A strains are the most prevalent clinical isolates and account for the majority of infections in AIDS patients, and serotype D strains are found predominant in Europe (43).

The mouse model of Cryptococcal meningitis/meningoencephalitis following intravenous inoculation was used to determine the hematogenous dissemination of C. neoformans to the brain as described previously (7, 8). C. neoformans strains grown on 1% yeast extracts, 2% peptone and 2% dextrose (YPD) agar were suspended in phosphate-buffered saline (PBS, pH 7.4) and counted with a hemocytometer to determine the yeast cell number. This suspension was also cultured on YPD agar plates, and colonies (CFUs) counted after 3 days of incubation at 30° C. as previously described (11). The inoculum size was confirmed by CFUs.

Figure 6:
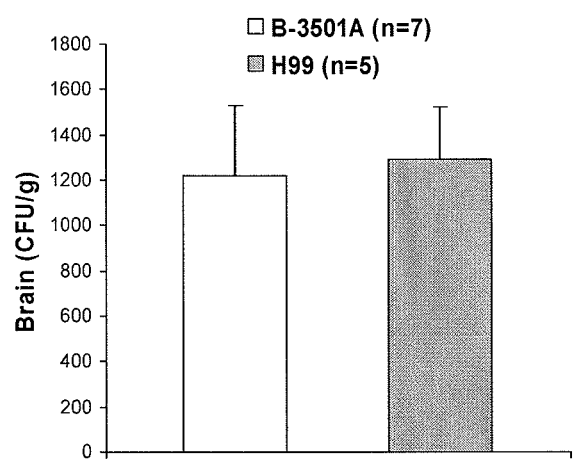
FIG. 6 shows Experimental *C. neoformans* meningitis/meningoencephalitis (defined as positive brain cultures) in BALB/c mice. At 24 hours after intravenous injection of *C. neoformans*, the blood specimens were obtained for CFU determinations. The animals were then perfused and the brains were removed, weighed, homogenized and cultured for CFU determinations (CFU/gm of brain). Results represent mean±SEM (no of animals).

Briefly, female BALB/c mice received $10^5$ yeast cells via the tail vein. 24 hours later, the blood specimens were obtained for determination of CFUs, and the animals perfused with sterile Ringer's solution until the perfused solution became colorless. The brains were removed, weighed, homogenized and cultured on YPD agar for determination of CFUs. Results are shown in FIG. 6.

As expected from our previous studies (7), C. neoformans strains B-3501A and H99 were completely cleared from the blood at 24 hours after intravenous injection and no viable yeasts were recovered from the blood. The CFUs in the brains were, therefore, most likely to represent the yeast cells that had penetrated into the brain and survived in the brain. As shown in FIG. 1, both strains of C. neoformans B-3501A and H99 were found to exhibit the similar ability to penetrate into the brain (based on CFUs/gm of brain).

B. Traversal of C. neoformans Across the Blood-Brain Barrier in the Mouse Model of C. neoformans Meningitis/Meningoencephalitis Following Intravenous Inoculation.

The mouse model of experimental meningitis/meningoencephalitis was used to examine the penetration of C. neoformans into the brain by cryosections and histopathological examinations (7).

Figure 7:
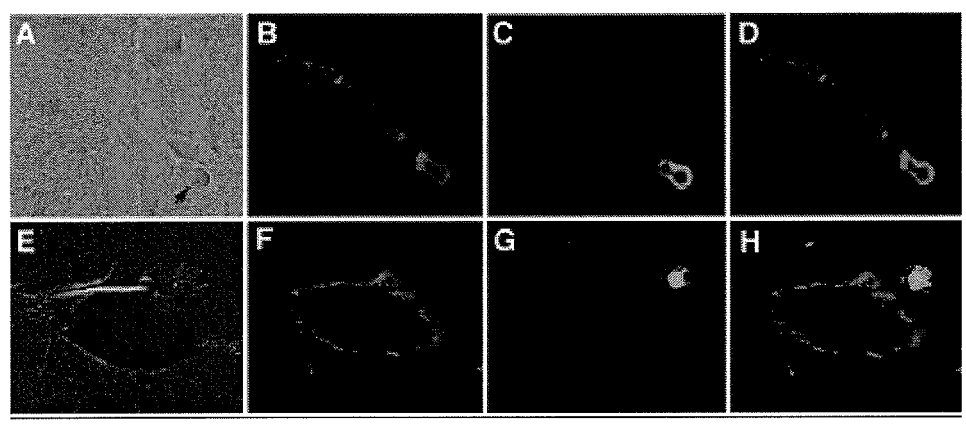
FIG. 7 shows demonstrations of *C. neoformans* in the brain cryosections following intravenous inoculation, A, B, C, D represent 3 hours post-injection and E, F, G, H represent 22 hours post-injection. A & E, phase contrast; B & F, anti- Factor VIII Rag antibody staining; C & G, Anti-GXM antibody staining; D & H overlay; arrow in A & E indicates yeast cells.

Briefly, BALB/c mice received $10^6$ CFU of C. neoformans B-3501 via the tail vein and were perfused with 4% formaldehyde in PBS at 3 and 22 hours after injection. The brains were removed and prepared for cryosections. The cryosections were stained with fluorescence conjugated anti-GXM (Cryptococcal polysaccharide capsule) antibody 18B7, specific for C. neoformans capsule, to visualize Cryptococcal cells, and anti-factor VIII Rag antibody to visualize the endothelial cells (FIG. 7).

As shown in FIG. 2, C. neoformans yeast cells which crossed the blood-brain barrier and were localized in close proximity to brain capillaries, could be detected at 3 hour post-injection (A-D). At 22 hours post-injection, some yeast cells had already migrated away from the vessel (E-H).

We also prepared the brain specimens for histopathology (7). Briefly, BALB/c mice received $10^6$ CFU of C. neoformans B-3501 via intravenous injection and were perfused with PBS followed by Trump fixative (Electron Microscopy Sciences) at 3 and 22 hours after injection. The brains were removed, embedded in glycerol methacrylate and sectioned in 2 µm thickness before staining with toluidine blue. In toluidine blue-stained sections, the brain tissue was stained blue, while C. neoformans cells stained pink.

Figure 8:
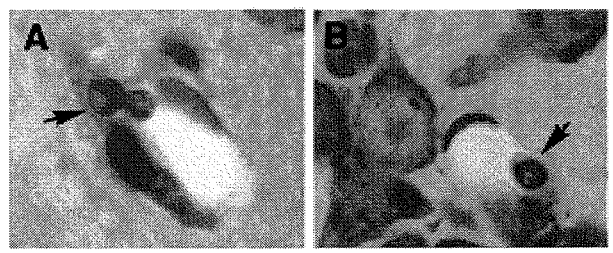
FIG. 8 shows a demonstration of *C. neoformans* (arrows in A and B) in the brain microvessels or brain microvascular endothelium in mice following intravenous inoculation.
Figure 9:
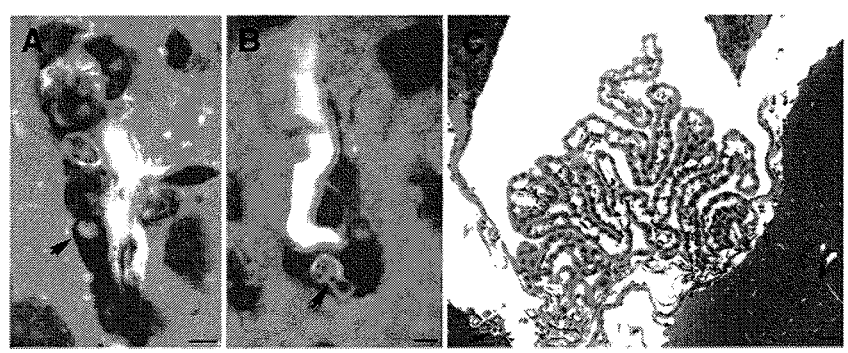
FIG. 9 shows histological sections of mouse brain stained with toluidine blue. (A and B) *C. neoformans* (arrows) lodged in endothelial cells of the brain microvessels. (C) Choroid plexus remained free of *C. neoformans*, while Cryptococcal lesions were seen in the nearby brain parenchyma (arrow). Scale bars=4 µm.

The sections prepared with the brains obtained 3 hours after intravenous injection showed very few C. neoformans cells which, when found, were always associated with the brain microvessels. Yeast cells were either closely associated with the endothelium or were in the process of escaping from the vessel lumen (FIGS. 8 and 9). Yeast cells were rarely detected in the brain parenchyma and none were observed in the choroid plexus. The choroid plexus was free of C. neoformans cells (FIG. 9). These findings are consistent with those of others (8-10), demonstrating that cerebral capillaries, not the choroid plexus are the portal of entry into the brain for circulating C. neoformans.

C. Development of In Vitro Model of the Blood-Brain Barrier by Isolation and Cultivation of Human Brain Microvascular Endothelial Cells (HBMEC).

Since the entry of C. neoformans into the brain occurred initially in the cerebral microvasculature, we next examined the interactions of C. neoformans with the in vitro model of the blood-brain barrier comprised of HBMEC.

HBMEC were isolated from small fragments of cerebral cortex as described previously (1-6). Briefly, brain specimens devoid of large blood vessels were homogenized in DMEM containing 2% bovine calf serum (DMEM-S) and centrifuged in 15% dextran in DMEM-S for 10 minutes at 1000×g. The pellets containing crude microvessels were further digested in a solution containing collagenase/dispase (1 mg/ml) for 1 hr at 37° C. Microvascular capillaries were isolated by adsorption to a column of glass beads and washing off the beads, and recovered in growth medium. Cell viability was greater than 95% as judged by trypan blue exclusion test. The human brain microvessels were plated on collagen coated dishes or glass coverslips and cultured in RPMI 1640 based growth medium at 37° C. in a humid atmosphere of 5% $CO_2$. The resulting HBMEC were positive for factor VIII, carbonic anhydrase IV, Ulex Europaeus Agglutinin I, took up acetylated low-density lipoprotein (AcLDL) and expressed gamma-glutamyl transpeptidase, demonstrating their brain endothelial characteristics. HBMEC were purified by FACS using fluorescently labeled DiI-AcLDL and found to be >99% pure after studying non-endothelial cell types. These HBMEC were split in a ratio of 1:3 twice a week and cultured without losing their specific characteristics up to passage 13.

Upon cultivation on collagen-coated Transwell inserts these HBMEC form a continuous lining of endothelial cells and exhibit morphologic and functional properties of tight junction formation as well as polar monolayer. These are shown by our demonstrations of tight junction proteins (such as ZO-1) and adherens junction proteins (such as β-catenin) and their spatial separation, limited permeability to inulin (m.w. 4,000), and development of high transendothelial electrical resistance (TEER) (1-6), a unique property of the brain microvascular endothelial monolayer compared to systemic vascular endothelium.

D. C. neoformans Traversal of HBMEC Monolayers.

Our next experiment was to examine the ability of C. neoformans strains to traverse the HBMEC monolayer as previously described (6, 7). C. neoformans strains B-3501A and H99 grown on YPD agar slant were resuspended in Hams-F12/M199 (1:1, v:v), 5% heat inactivated fetal bovine serum (experimental medium) and 1% human serum.

Briefly, HBMEC were cultured on 12 mm-diameter, collagen-coated Transwell polycarbonate tissue culture inserts with a pore size of 12 µm (Corning Costar Corp) for at least 5 days (7). This in vitro blood-brain barrier model allows separate access to the upper chamber (blood side) and lower chamber (brain side) and permits mimicking of C. neoformans penetration into the brain. $10^7$ yeast cells were added to the upper chamber, and the monolayers were incubated at 37° C.

Our previous studies revealed that transcytosis of C. neoformans across the HBMEC monolayer was evident over a 9 hr incubation period (7). At 9 hr of incubation, 1 ml sample was taken from the lower chamber, diluted and cultured for CFU determination. Since the yeast cells do not divide well in the culture medium (T½ of approximately 20 hours), the CFU numbers of C. neoformans in the lower chamber are most likely due to the passage of C. neoformans across HBMEC monolayer. The results were calculated as the percent traversal frequency of inoculum: [(number of C. neoformans crossed)/(number of C. neoformans inoculated)]×100. (FIG. 10).

Figure 10:
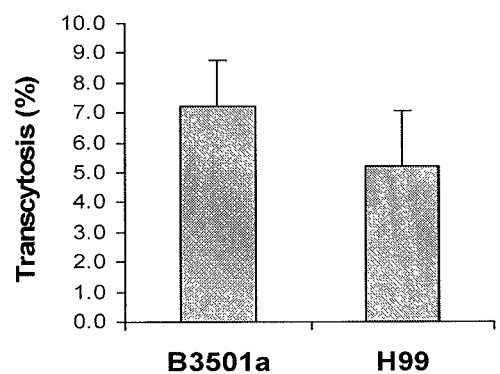
FIG. 10 shows transcytosis (mean±SEM) of *C. neoformans* strains B-3501A and H99 across the HBMEC monolayers. Results represent two separate experiments in triplicate.

As shown in FIG. 10, both strains B-3501A and H99 exhibited the similar ability to cross the HBMEC monolayers. Exposure of HBMEC to C. neoformans strains B-3501A and H99 did not affect the HBMEC viability, as determined by live/dead stain (Molecular Probes).

We also examined the effect of C. neoformans traversal on the HBMEC monolayer integrity, as measured by passive diffusion of $^3$H-inulin and TEER at the end of the transcytosis experiment as described previously (7).

As shown in FIG. 11, inulin permeability of the HBMEC monolayers with and without incubation with B-3501 cells showed no significant differences. Also, TEER values remained similar between the HBMEC monolayers with and without B-3501. Taken together, these findings illustrate that *C. neoformans* yeast cells crossed the HBMEC monolayers without affecting the integrity of HBMEC monolayers.

E. Transmission (TEM) and Scanning Electron Microscopy (SEM) Studies of *C. neoformans* Interaction with HBMEC.

To visualize the interaction of *C. neoformans* with HBMEC, our next experiment was to examine the morphological changes that occurred on the surface of HBMEC upon exposure to *C. neoformans* by electron microscopy (7).

HBMEC were seeded on gelatin/collagen coated glass cover slips, grown to confluence and exposed to *C. neoformans* strain B-3501. The monolayers were washed with culture medium and prepared for TEM according to a modified method of McCaffery, et al., (44). Briefly, HBMEC were fixed with ice-cold 100 mM cacodylate buffer containing 3% formaldehyde, 1.5% glutaraldehyde, 5 mM $CaCl_2$, pH7.4. The cell monolayer and collagen film were subsequently post-fixed in Palade's OsO4 for 1 hr at 4° C., en bloc stained in Kellenberger's uranyl acetate, dehydrated through a graded series of ethanol and embedded in Spurr resin. Ultrathin sections were cut on a Leica UCT ultramicrotome, collected onto 400 mesh thin bar grids and post stained in uranyl acetate and lead citrate. Sections were viewed using a Philips EM 420 transmission electron microscope. Images were recorded using a Soft Imaging System Megaview III digital camera and analySIS software.

For SEM, cells were grown as described for TEM, but fixed in 2% glutaraldehyde 2% paraformaldehyde in 0.1M Hepes buffer containing 3 mM $CaCl_2$, pH 7.3 at 4° C. for a minimum of 30 mins. Thereafter, HBMEC were rinsed in Hepes buffer× 3 for 10 mins at 4° C. and postfixed in 1% $OsO_4$, 0.8% $KFeCN_6$ in 0.1M $CaCl_2$, pH 7.3 for 1 hr on ice. After rinsing in D-$H_2$O×2 for 5 mins, HBMEC were en-bloc stained with 2% uranyl acetate in D-$H_2$O for 2 hr in the dark. HBMEC were dehydrated in a graded alcohol series till final 100% ethanol. Subsequently, samples were infused with hexamethyldislazane (Polysciences) for 10 mins, allowed to airdry on #1 Whatman filterpaper. Samples were then affixed onto SEM-stubs and evaporated with 5 nm chromium in a Denton DV-502A high vacuum evaporator operating at 50 mAmps and 2×10$^7$ Torr. Samples were viewed and digitized on a Leo 1530 FESEM SEM, operating at 1 KV.

Figure 12:
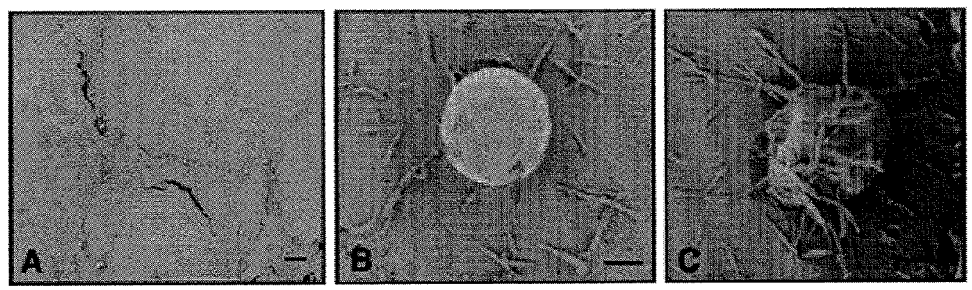
FIG. 12 shows a SEM of HBMEC infected with *C. neoformans* strain B-3501. (A) Surface of HBMEC at time 0 (control). (B) Microvilli-like projections were observed 15 min after addition of strain B-3501 to HBMEC. (C) Microvilli-like projections are covering yeast cells at 30 min. Scale bar=4 µm.

As shown in FIG. 12, prior to incubation with *C. neoformans*, the HBMEC monolayers showed smooth cell surface with very few microvilli-like membrane protrusions (A). After 15-30 min incubation with *C. neoformans*, SEM showed that internalizing *C. neoformans* was associated with microvilli-like protrusions at the entry site on the surface of HBMEC monolayers (B and C), suggesting that *C. neoformans* induces host cell actin cytoskeleton rearrangements for the initiation of entry into HBMEC.

Figure 13:
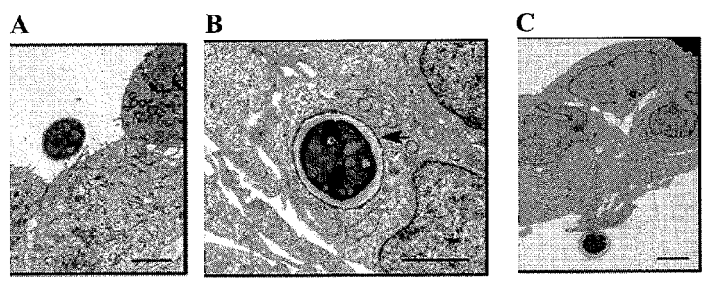
FIG. 13 shows a TEM examination of HBMEC infected with *C. neoformans*. (A) Formation of microvilli-like projections upon exposure to strain B-3501. (B) B-3501 completely internalized in the vacuole of HBMEC (arrow) (C) B-3501 at the basolateral side of HBMEC after crossing. Scale bar=4 µm.

Our TEM experiments with the strain B-3501 revealed that upon exposure to *C. neoformans*, HBMEC monolayers exhibited microvilli-like membrane protrusions within 15-30 min (FIG. 13A). *C. neoformans* was found intracellularly in membrane bound vacuoles and no free *C. neoformans* cells were seen in the cytoplasm (FIG. 13B). Some yeast cells were seen at the basolateral side of the HBMEC monolayer after 6 hr of incubation (FIG. 13C), suggesting a complete crossing of HBMEC by this time.

Taken together, these findings indicate that *C. neoformans* internalization and traversal of the HBMEC monolayers is associated with the host cell actin cytoskeleton rearrangements.

F. Use of Pharmacological Inhibitors/Antagonists for Determination of the Host Signaling Molecules Involved in *C. neoformans* Traversal of the HBMEC Monolayers.

As shown above, our previous studies have shown that traversal of meningitis-causing microorganisms across the HBMEC monolayers involves cytosolic phospholipase $A_{2\alpha}$ ($cPLA_{2\alpha}$) (1, 2, 45).

Figure 14:
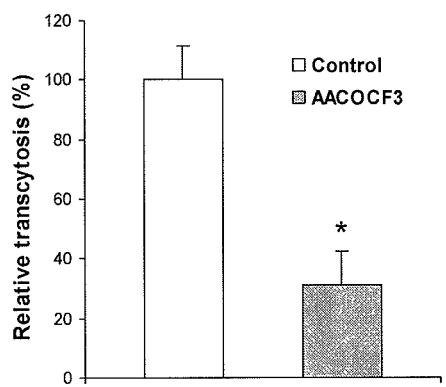
FIG. 14 shows *C. neoformans* B-3501A traversal of HBMEC monolayer was significantly decreased by AACOCF3 at 20 µM compared to vehicle control (0.1% ethanol, which was set at 100%). Data represent mean±SEM of two separate experiments done in triplicate. *p<0.05 compared to vehicle control.

We initially examined the role of host $cPLA_{2\alpha}$ in *C. neoformans* traversal of the HBMEC monolayer by using a pharmacological inhibitor of $cPLA_{2\alpha}$ (AACOCF3). Briefly, HBMEC monolayers were pretreated with AACOCF3 at 20 µM (the concentration which inhibited $cPLA_{2\alpha}$ activity in HBMEC in our previous study with *E. coli* invasion of HBMEC, 45) and then processed for transcytosis assays with *C. neoformans* strain B-3501A by the method described in our Studies section D. Transcytosis frequency (%) was expressed as relative frequency compared to transcytosis frequency with vehicle control (0.1% ethanol), and the results are shown in FIG. 14.

AACOCF3 at 20 µM did not affect the integrity of the HBMEC monolayers, as assessed by TEER measurements before and after transcytosis assays.

Figure 15:
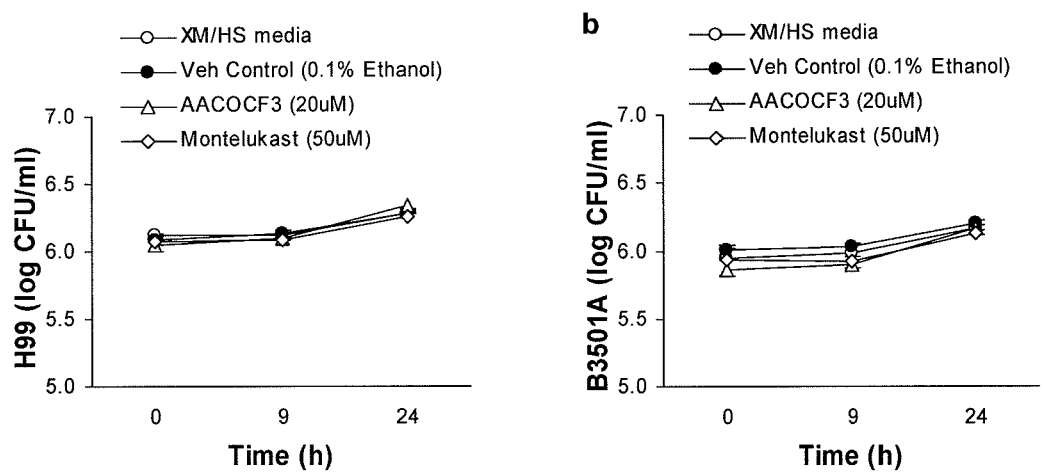
FIG. 15 shows growth of *C. neoformans* strains H99 (a) and B3501A (b) was not affected by AACOCF3 (a cPLA2α inhibitor) and montelukast (a CysLT1 antagonist), compared to experimental medium with human serum (XM/HS) and vehicle control. Each experiment was performed in triplicate.

AACOCF3 at 20 µM also did not affect growth of *C. neoformans*, as shown in FIG. 15. Briefly, *C. neoformans* strains were grown in experimental medium and 1% human serum with AACOCF3 (20 µM) or montelukast (50 µM, a CysLT1 antagonist) or vehicle control (0.1% ethanol) at 37° C., 5% $CO_2$ incubator, and CFUs were determined at 0, 9 and 24 h incubation time.

$cPLA_{2\alpha}$ mediates agonist-induced arachidonic acid release for eicosanoid production such as leukotrienes (LTs) (32). LTs comprise a group of biologically potent lipid mediators synthesized by 5-lipoxygenase (5-LO) from 20-carbon polyunsaturated fatty acid, predominantly arachidonate. The enzyme 5-LO, in conjunction with 5-LO-activating protein (FLAP), oxygenates arachidonic acid to LTA4. This unstable intermediate can be hydrolyzed to form the dihydroxyeicosatetraenoate (LTB4) or conjugated with glutathione to form the cysteinyl LTs (LTC4, LTD4 and LTE4) (11).

Both of these terminal LTs are biologically active in that specific G-protein coupled receptors (GPCRs) recognize these chemical structures and receptor recognition initiates specific intracellular signaling cascades. The leukotriene GPCRs have been designated BLT-1 and BLT-2 that bind to LTB4 specifically, and CysLT1 and CysLT2 which are known to bind to the CysLTs (LTC4, LTD4 and LTE4) (11, 49).

We next examined which class of LTs is involved in *C. neoformans* traversal of the HBMEC monolayers using montelukast (the CysLT1 antagonist) as described above. Briefly, HBMEC monolayers were pretreated with montelukast in varying concentrations and then processed for transcytosis assays. The results were expressed as relative frequency compared to transcytosis frequency with vehicle control (0.1% ethanol).

Montelukast at 50 µM did not affect the integrity of the HBMEC monolayers, as measured by TEER, and also did not affect the growth of *C. neoformans*, as shown in FIG. 10. Taken together, these findings indicate that host $cPLA_{2\alpha}$ and cysteinyl LTs contribute to *C. neoformans* traversal of the HBMEC monolayers.

G. Use of Animal Models for Elucidating the Roles of Host Signaling Molecules in *C. neoformans* Penetration into the Brain.

Figure 17:
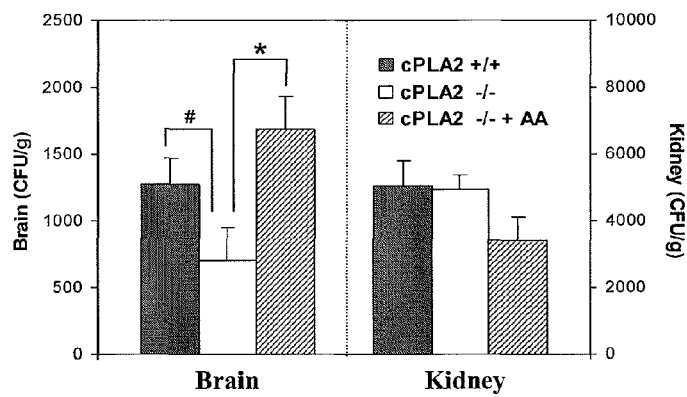
FIG. 17 shows the role of host $cPLA_{2\alpha}$ in *C. neoformans* penetration into the brain. *C. neoformans* strain B-3501A penetration into the brain was significantly less in $cPLA_{2\alpha}$-/- mice compared to the wild type animals, while the penetration into the kidneys did not differ between the two groups of animals. Exogenous arachidonic acid (AA) restored *C. neoformans* penetration into the brain of $cPLA_{2\alpha}$-/- mice to the level of the wild type. Results (mean±SEM) represent 4 animals per each group. #,*, p<0.05.
Figure 18:
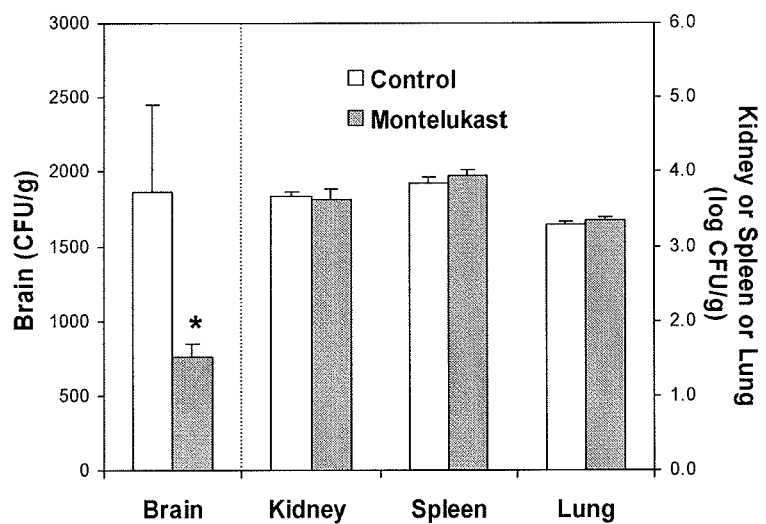
FIG. 18 shows that Montelukast significantly (p<0.05) decreased *C. neoformans* strain H99 penetration into the brain in BALB/c mice, while it did not affect the penetration into the kidney, spleen and lung. Results (mean±SEM) represent six animals per each group. *p<0.05

Our next Experiment was to examine whether the above-mentioned signaling molecules involved in *C. neoformans* traversal of the HBMEC monolayers are relevant to *C. neoformans* penetration into the brain, using the mouse model of experimental *C. neoformans* meningitis/meningoencephalitis as described in Additional Studies section A.

cPLA$_{2\alpha}$. We examined the role of host cPLA2α in *C. neoforman* strain B-3501A penetration into the brain by studying cPLA$_{2\alpha}$-/- mice as compared to their strain-matched wild type mice. Each animal received $10^5$ yeast cells via the tail vein. 24 hours later, the blood specimens were obtained for determination of CFUs, and the animals perfused with sterile Ringer's solution until the perfused solution became colorless. The brains as well as the kidneys were removed, weighed, homogenized and cultured for determinations of CFUs. The results are shown in FIG. 17.

As expected, *C. neoformans* strain B-3501A was completely cleared from the blood at 24 hours after intravenous injection and no viable yeasts were recovered from the blood of both cPLA$_{2\alpha}$-/- and wild type mice. The yeast counts recovered from the brains (CFU/gm) were significantly less in cPLA$_{2\alpha}$-/- mice than in their wild type animals (FIG. 17). In contrast, the yeast counts recovered from the kidneys (CFUs/gm) did not differ between the two groups of cPLA$_{2\alpha}$-/- and wild type animals. These in vivo findings suggest that host cPLA$_{2\alpha}$ contributes to *C. neoformans* penetration into the brain, but not into non-brain organs such as kidneys.

cPLA$_{2\alpha}$ selectively liberates arachidonic acid from the sn-2 position of membrane phospholipids (32). We next examined whether exogenous acachidonic acid restores the ability of *C. neoformans* to penetrate into the brain of cPLA$_{2\alpha}$-/- mice. Intravenous administration of arachidonic acid (1.2 μg/mouse in 50 μl in PBS) 30 mins before *C. neoformans* injection significantly enhanced *C. neoformans* penetration into the brain to the level observed in the wild type mice, but did not affect the yeast counts in the kidneys compare to the vehicle control (FIG. 17).

The enhancement of *C. neoformans* penetration into the brain of cPLA$_{2\alpha}$-/- mice by arachidonic acid was not accompanied by any change in the blood-brain barrier permeability, as assessed by extravasation of systemically administered Evans blue dye into the brain (see the Experimental Design and Methods). These findings are consistent with those of our in vitro studies, where *C. neoformans* transcytosis of the HBMEC monolayers did not result in any change in the integrity of HBMEC monolayers.

Taken together, these findings demonstrate for the first time that host cPLA$_{2\alpha}$ activity contributes to *C. neoformans* traversal of the HBMEC monolayers and penetration specifically into the brain.

Figure 16:
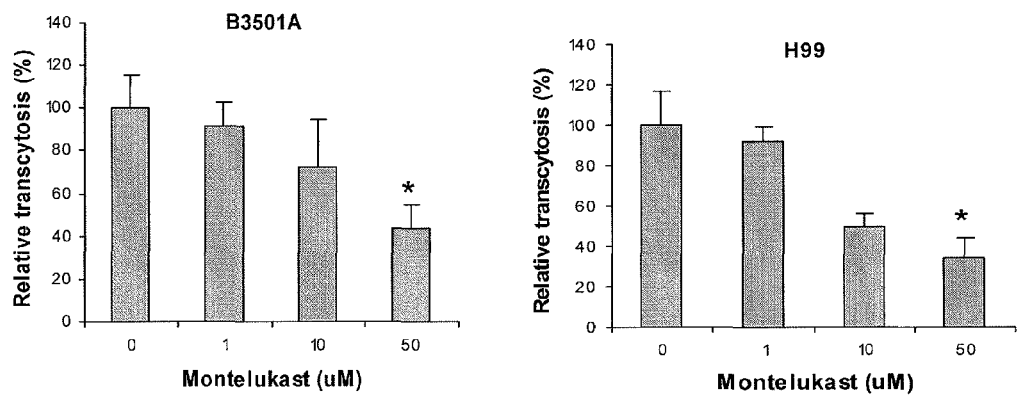
FIG. 16 shows that montelukast inhibited traversal of *C. neoformans* strains B-3501A and H99 across the HBMEC monolayer in a dose-dependent manner. Inhibition by montelukast at 50 µM was significant compared to the vehicle control (0.1% ethanol), which was set at 100%. Data represent mean±SEM of two separate experiments done in triplicate. *p<0.05 compared to the vehicle control (0 µM).

Cysteinyl LTs. Our studies showed that montelukast (the CysLT1 antagonist) exhibited a dose-dependent inhibition of *C. neoformans* traversal of the HBMEC monolayers (FIG. 16), suggesting that host cell-derived cysteinyl LTs may play a role in *C. neoformans* traversal of the blood-brain barrier and penetration into the brain.

We next examined whether cysteinyl LTs contribute to *C. neoformans* penetration into the brain using the CysLT1 antagonist (montelukast). Briefly, montelukast (100 μg/mouse, a dose which is shown to antagonize CysLT1 in mice) was injected into the tail vein of BALB/c mice 15 min before and 6 hrs after intravenous injection of *C. neoformans* strain H99, and the specimens of blood, brain, spleen, kidney and lung were obtained at 24 hours of *C. neoformans* injection for determinations of CFUs as described above.

As shown before, no viable yeasts were recovered from the blood at 24 hours after intravenous inoculation in animals receiving montelukast or vehicle control. The yeast counts recovered from the brains (CFU/gm) were significantly (p<0.05) less in the recipients of montelukast compared to the recipients of the vehicle control group (0.1% ethanol). In contrast, the yeast counts recovered from the kidney, spleen and lung specimens did not differ significantly between the two groups. These findings suggest that host cell-derived cysteinyl LTs are likely to contribute to *C. neoformans* traversal of the HBMEC monolayers and penetration specifically into the brain.

H. Mouse Model of *C. neoformans* Meningitis/Meningoencephalitis Following Intratracheal Inoculation.

As indicated before, *C. neoformans* is commonly acquired by inhalation, and extrapulmonary dissemination leads to infection of the bloodstream and subsequent dissemination to the CNS, resulting in meningitis/meningoencephalitis (15-19).

Our next study was to determine whether the above-mentioned concept derived with intravenous inoculation model is relevant to *C. neoformans* penetration into the brain following intratracheal inoculation as described previously (9, 37). Both intravenous and intratracheal inoculation models measure the ability of *C. neoformans* to penetrate into the brain from hematogenous dissemination, but the intravenous inoculation model measures the ability of *C. neoformans* to disseminate throughout the body, while the intratracheal inoculation model measures the ability to disseminate from the lungs, e.g., the ability of the yeasts that disseminate from the lung to cross the blood-brain barrier.

Figure 19:
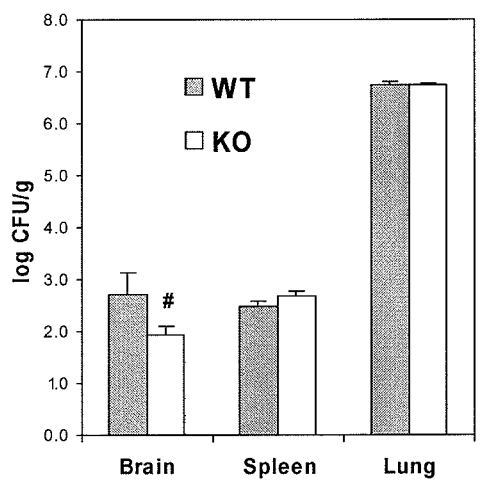
FIG. 19 shows the role of host 5-LO in *C. neoformans* penetration into the brain following intratracheal inoculation. *C. neoformans* strain H99 penetration into the brain was significantly (p<0.05) less in 5-LO-/- mice compared to the wild type. In contrast, the yeast counts recovered from the lungs and spleen did not differ between the two groups of animals. Results (mean±SEM) represent 6 animals per each group. #p<0.05.

Briefly, 5-LO-/- and strain-matched (129SvEv) wild type mice were anesthetized by intraperitoneal injection of pentobarbital sodium and trachea was exposed by small incision through the skin. A bent 30-gauge needle attached to a tuberculin syringe was used to inject $10^5$ cells of *C. neoformans* strain H99 in 30 μl into the trachea and lungs. The skin was closed with cyanoacrylate adhesive and the mice were recovered with no visible trauma. At 7 days after infection, the specimens of blood, brain, spleen and lung were obtained for determinations of CFUs as described above. The results are shown in FIG. 19.

As shown before, no viable yeasts were recovered from the blood of both 5-LO-/- and wild type mice at 7 days after intratracheal inoculation. The yeast cells recovered from the brains (CFU/gm) were significantly (p<0.05) less in 5-LO-/- mice than in wild type mice, while the yeast counts recovered from the lungs and spleen did not differ significantly between the two groups.

Taken together, these findings indicate that 5-LO is likely to contribute to *C. neoformans* traversal of the blood-brain barrier and penetration specifically into the brain, following intravenous as well as intratracheal inoculations.

Based on the findings derived from the above-mentioned studies, inhibition and/or blockade of host signaling molecules involved in microbial traversal of the blood-brain barrier, such as cPLA$_{2\alpha}$, 5-LO and cysteinyl LTs can be used to inhibit *C. neoformans* penetration into the brain.

LITERATURE CITED

All Incorporated by Reference Herein

Kim K S. Neurological diseases: Pathogenesis of bacterial meningitis: from bacteremia to neuronal injury. Nature Rev. Neurosci. 4, 376-85:2003.

Kim K S. Mechanisms of microbial traversal of the blood-brain barrier. Nature Rev Microbiol 6:625-634, 2008

Stins M F, Gilles F and Kim K S. Selective expression of adhesion molecules on human brain microvascular endothelial cells. J. Neuroimmunol. 76, 81-90:1997.

Ruffer C, Strey A, Janning A, Kim K S and Gerke V. Cell-cell junctions of dermal microvascular endothelial cells contain tight and adherens junction proteins in spatial proximity. Biochemistry 43:5360-5369, 2004.

Kim, Y V, DiCello F, Hillaire C S and Kim K S. Protease-activated receptors of human brain microvascular endothelial cells: Expression and differential $Ca^{2+}$ signaling induced by thrombin and protease-activated receptor-1 activating peptide. Am J Physiol Cell Physiol 286:C31-42, 2004.

Stins M F, Badger J and Kim K S. Bacterial invasion and transcytosis in transfected human brain microvascular endothelial cells. Micro. Pathogenesis 30, 19-28:2001.

Chang Y C, Stins M F, McCaffery M J, Miller G F, Pare D R, Dam T, Paul-Satyasee M, Kim K S, Kwon-Chung K J. Cryptococcal yeast cells invade the central nervous system via transcellular penetration of the blood-brain barrier. Infect Immun 72:4985-4995, 2004.

Chretien F, Lortholary O, Kansau I, Neuville S, Gray F and Dromer F. Pathogenesis of cerebral *Cryptococcus neoformans* infection after fungemia. J. Infect. Dis. 4, 522-30:2002.

Olszewski M A, Noverr M C, Chen G-H, Toews G B, Cox G M, Perfect J R and Huffnagle G B. Urease expression by *Cryptococcus neoformans* promotes microvascular sequestration, thereby enhancing central nervous system invasion. Am. J. Pathol. 164, 1761-71:2004.

Charlier C, Chretien F, Baudrimont M, Mordelet E, Lortholary O, and Dromer F. Capsule structure changes associated with *Cryptococcus neoformans* crossing of the blood-brain barrier. Am. J. Pathol. 166:421-32, 2005.

Peters-Golden M, Henderson W R. Leukotrienes. N Eng J Med 357:1841-1854, 2007

Montuschi P, Sala A, Dahlen S, Folco G. Pharmacological modulation of the leukotriene pathways in allergic airways disease. Drug Discovery Today 12:404-412, 2007.

Evans J F, Ferguson A D, Mosley R T, Hutchinson J H. What's all the FLAP about ?: 5-lipoxygenase-activating protein inhibitors for inflammatory diseases. Trends Pharmacological Sci 29:72-78, 2008.

Funk, C. D. (2005). Leukotriene modifiers as potential therapeutics for cardiovascular disease. Nat. Rev. Drug Discov. 4, 664-672.

Perfect J R and Casadevall A. *Cryptococcus*. Infect. Dis. Clin. North Am. 4, 837-74:2002.

Eisenman H C, Casadevall A, McClelland E E. New insights on the pathogenesis of invasive *Cryptococcus neoformans* infection. Curr Infect Dis Reports. 9:457-464, 2007

Chuck S L, Sande and M A. Infections with *Cryptococcus neoformans* in the acquired immunodeficiency syndrome. N. Engl. J. Med. 321, 794-9:1989.

Powderly W G. Cryptococcal meningitis and AIDS. Clin. Infect. Dis. 17, 837-42:1993.

Mitchell T G and Perfect J R. *Cryptococcus* in the era of AIDS—100 years after the discovery of *Cryptococcus neoformans*. Clin. Microbiol. Rev. 4, 515-48:1995.

Jarvis J N, Harrison T S. HIV-associated cryptococcal meningitis. AIDS 21:2119-2129, 2007

Chin S, Rozycki G, Pugatch D and Harwell J I. Aetiology of meningitis in HIV-infected patients in a referral hospital in Phnom Penh, Cambodia. Int. J. STD AIDS. 15, 48-50:2004.

Hakim J G, Gangaidzo I T and Heyderman R S. Impact of HIV infection on meningitis in Harare, Zimbabwe: a prospective study of 406 predominantly adult patients. AIDS 14, 1401-7:2000.

Gordon S B, Walsh A L and Chaponda M. Bacterial meningitis in Malawian adults: pneumococcal disease is common, severe, and seasonal. Clin. Infect. Dis. 53-7:2000.

Mussini C, Pezzotti P, Miró J M, et al. Discontinuation of maintenance therapy for cryptococcal meningitis in patients with AIDS treated with highly active antiretroviral therapy: an international observational study. Clin Infect Dis 2004; 38:565-71.

Saag M S, Graybill R J, Larsen R A, et al. Practice guidelines for the management of cryptococcal disease. Infectious Diseases Society of America. Clin Infect Dis 2000; 30:710-8.

Vibhagool A, Sungkanuparph S, Mootsikapun P, Chetchotisakd P, Tansuphaswaswadikul S, Bowonwatanuwong C, Ingsathit A. Discontinuation of secondary prophylaxis for cryptococcal meningitis in human immunodeficiency virus-infected patients treated with highly active antiretroviral therapy: a prospective, multicenter, randomized study. Clin Infect Dis 2003; 36:1329-31

Lee S C, Dickson D W and Casadevall A. Pathology of Cryptococcal meningoencephalitis: analysis of 27 patients with pathogenetic implications. Hum. Pathol. 8, 839-47:1996.

Lee S C, Casadevall A and Dickson D W. Immunohistochemical localization of capsular polysaccharide antigen in the central nervous system cells in cryptococcal meningoencephalitis. Am. J. Pathol. 4, 1267-74:1996.

Neuville S, Dromer F, Chretien F, Gray F, Lortholary O. Physiopathology of meningoencephalitis caused by *Cryptococcus neoformans*. Ann. Med. Intern. 5, 323-8:2002.

Cossart P and Sansonetti P J. Bacterial invasion: the paradigms of enteroinvasive pathogens. Science 304, 242-8:2004.

Knodler L A, Celli J, and Finlay B B. Pathogenic trickery: deception of host cell processes. Nat. Rev. Mol. Cell Biol. 2:578-88, 2001.

Ghosh M, Tucker D E, Burchett S A, Leslie C C. Properties of the group IV phospholipase A2 family. Prog Lipid Res 45:487-510, 2006

Kandzari D E, Chen J, Goldschmidt-Clermont P J. Regulation of the actin cytoskeleton by inositol phospholipids pathways. Subcell Biochem 26:97-114, 2006

Tsitsigiannis D I, Keller N P. Oxylipins as developmental and host-fungal communication signals. Trend Microbiol 15:109-118, 2007

Erb-Downward J R, Huffnagle G B. *Cryptococcus neoformans* produces authentic prostaglandin E2 without a cylcooxygenase. Enkaryot Cell 6:346-350, 2007

Noverr M C, Phare S M and Toews G B. Pathogenic yeasts *Cryptococcus neoformans* and *Candida albicans* produce immunomodulatory prostaglandins. Infect. Immun. 69, 2957-63:2001.

Noverr M C, Cox G M, Perfect J R and Huffnagle G B. Role of PLB1 in pulmonary inflammation and Cryptococcal eicosanoid production. Infect. Immun. 1538-1547:2003.

Santangelo R, Zoellner H, Sorrell T, Wilson C, Donald C, Djordjevic J, Shounan Y and Wright L. Role of extracellular phospholipases and mononuclear phagocytes in dissemination of Cryptococcosis in a murine model. Infec. Immun. 72, 2229-2239:2004

Kozel T R. Virulence factors of *Cryptococcus neoformans*. Trends Microbiol. 8, 295-9:1995.

Reiss T F, Sorkness C A, Stricker W, Botto, A, Busse W W, Kundu S, Zhang J. Effects of montelukast (MK-0476); a potent cysteinyl leukotriene receptor antagonist, on bronchodilation in asthmatic subjects treated with and without inhaled corticosteroids. Thorax 52:45-48, 1997.

Capra V, Thompson M D, Sala A, Cole D E, Folco G, Rovati G E. Cysteinyl leykotrienes and their receptors in asthma and other inflammatory diseases: critical update and emerging trends. Med Res Rev 27:469-527, 2007.

Kemp J P. Advances in the management of pediatric asthma: A review of recent FDA drug approvals and label updates. J Asthma 42:615-622, 2005.

Casadevall A, Perfect J R. *Cryptococcus neoformans*. Washinton, D.C. American Society for Microbiology Press, 1998.

McCaffery J M and Farquhar M G. Localization of GTPases by indirect immunofluorescence and immunoelectron microscopy. Methods Enzymol. 257, 259-79:1995.

Das A, Asatryan L, Reddy M A, Wass C A, Stins M, Joshi S, Bonentre J V, Kim K S. Differential role of cytosolic phospholipase A2 in the invasion of brain microvascular endothelial cells by *Escherichia cells* and *Listeria monocytogenes*. J Infect Dis 184:732-37, 2001

Kim Y, Pearce D, Kim K S. Ca2+/Calmodulin-dependent invasion of the human brain microvascular endothelial cells by *Escherichia coli* K1. Cell & Tissue Res 332:427-433, 2008

Kaya M, Kayayci R, Kucuk M, Arican N, Elmas I, Kudat H, Korkut F. Effect of losartan on the blood-brain barrier permeability in diabetic hypertensive rats. Life Sci. 73, 3235-44, 2003.

Pu H, Hayashi K, Andras I E, Eum S Y, Henning B, Toborek M. Limited role of COX-2 in HIV Tat-induced alterations of tight junction protein expression and disruption of the blood-brain barrier. Brain Res. 1184, 333-44, 2007.

Murphy R C, Gijon M A, Biosynthesis and metabolism of leukotrienes. Biochem J 405:379-395, 2007

Loftus B J, Fung E, Roncaglia P, et al. The genome of the basidiomycetous yeast and human pathogen *Cryptococcus neoformans*. Science 307:1321-4, 2005.

Qiao J, Huang F, Naikawadi R P, Kim K S, Said T, Lum H. Lysophosphatidylcholine impairs endothelial barrier function through the G-protein coupled receptor, GPR4. Am J Physiol Lung Cell Mol Physiol. 291:L91-L101, 2006

Coyne C B, Kim K S, Bergelson J M. Poliovirus entry into human brain microvascularendothelial cells requires receptor-induced activation of SHP-2. EMBO J 26:4016-4028, 2007

Pavicevic Z, Leslei C C, Malik K U. cPLA2 phosphorylation at serine-515 and serine-505 is required for arachidonic acid release in vascular smooth muscle cells. J Lipid Res 49:724-737, 2008

Hefner Y, Borsch-Haubold A G, Murakami M, Wilde J I, Pasquet S, Schieltz D, Ghomashchi F, Yates J R, Armstrong C G, Paterson A, Cohen P, Fukunaga R, Hunter T, Kudo I, Watson S P, Gelb M H. Serine 727 phosphorylation and activation of cytosolic phosholipase, A2 by MNK1-related protein kinases. J Biol Chem 275:37542-37551, 2000

Tian W, Wijewickrama G T, Kim J H, Das S, Tun M P, Gokhale N, Jung J W, Kim K P, Cho W. Mechanism of regulation of group IVA phospholipase A2 activity by serine 727 phosphorylation. J Biol Chem 283:3960-3971, 2008

Shin S, Kim K S. RhoA and Rac1 contribute to type III group B streptococcal invasion of human brain microvascular endothelial cells. Biochem Biophys Res Commun 345: 538-542, 2006

Shin S, Maneesh P, Lee J, Romer L and Kim K S. Focal adhesion kinase is involved in type III group B streptococcal invasion of human brain microvascular endothelial cells. Microb Pathogenesis 41:168-173, 2006

Example 4

GBS and *E. coli* Additional Studies

Neonatal bacterial meningitis is associated with high mortality and morbidity. Group B *Streptococcus* (GBS) and *Escherichia coli* (*E. coli*) are the two most common bacteria causing neonatal meningitis. Several lines of evidence from experimental animal models of hematogenous GBS and *E. coli* meningitis as well as from human cases of neonatal GBS and *E. coli* meningitis indicate that GBS and *E. coli* penetrate into brain initially in the cerebral vasculature, but it is incompletely understood how circulating GBS and *E. coli* penetrate into the brain. The blood-brain barrier protects the brain from any microbes and toxins circulating in the blood. Recent studies, however, have shown that meningitis-causing microorganisms including GBS and *E. coli* traverse the blood-brain barrier as live organisms. We have developed the innovative in vitro blood-brain barrier model by isolation and cultivation of human brain microvascular endothelial cells (BMEC). Upon cultivation on collagen-coated Transwell inserts the human BMEC monolayers exhibit morphological and functional properties of tight junction formation and polar monolayer. It appears that GBS and *E. coli* invasion of the human BMEC monolayers occurs as the result of their interactions with the blood-brain barrier, involving specific host cell signal transduction pathways. Our findins are supported by our studies, where host cytosolic phospholipase A2α (cPLA2α), 5-lipoxygenase (5-LO) and leukotrienes (LTs) are shown to contribute to GBS and *E. coli* invasion of the human BMEC monolayers and penetration into the brain. cPLA2α has been shown to be involved in the development of arthritis, bone resorption and pulmonary fibrosis, while LTs have been involved in respiratory diseases, allergic diseases and cardiovascular diseases, but the roles of cPLA2α and LTs in microbial penetration of the blood-brain barrier have not been explored.

One distressing aspect of neonatal bacterial meningitis is limited improvement in the mortality and morbidity attributable to advances in antimicrobial chemotherapy and supportive care (1-3). Both clinical and experimental data indicate limited efficacy with antimicrobial chemotherapy alone (1-5). Inadequate knowledge of the pathogenesis has contributed to high mortality and morbidity.

Group B *streptococcus* (GBS) and *Escherichia coli* (*E. coli*) are the two most common bacteria that cause neonatal meningitis (1-5). Most cases of GBS and *E. coli* meningitis develop as a result of hematogenous spread (6-9). Several lines of evidence from experimental animal models and human cases with GBS and *E. coli* meningitis indicate that GBS and *E. coli* invasion into the brain follows high-levels of bacteremia and cerebral capillaries are the portal of entry into the brain (7-10).

As discussed above, we have developed an innovative in vitro model of the blood-brain barrier by isolation and cultivation of human brain microvascular endothelial cells (BMEC) (11-14). Our human BMEC, upon cultivation on collagen-coated Transwells, exhibit spatial organization of tight and adherens junction proteins as well as high transendothelial electrical resistance, a unique property of the BMEC monolayer (11-14).

We have shown that serotype III GBS and *E. coli* K1 strains, which account for the majority of cerebrospinal fluid (CSF) isolates from neonates with meningitis invade human BMEC monolayers (15, 16), as shown by internalization of type III GBS and *E. coli* K1 into human BMEC by our transmission electron microscopy studies (1-3, 16, 17). The mechanisms involved in type III GBS and *E. coli* K1 invasion of human BMEC monolayers, however, remain incompletely understood.

Our Additional Studies below showed that host cell cytosolic phospholipase $A_{2\alpha}$ ($cPLA_{2\alpha}$) and 5-lipoxygenase (5-LO) are likely to be involved in type III GBS and *E. coli* K1 invasion of human BMEC monolayers and penetrations into the brain. Leukotrienes (LTs) comprise a group of biologically potent lipid mediators synthesized by 5-LO (18, 19). The roles of $cPLA_{2\alpha}$ and LTs in microbial traversal of the blood-brain barrier has not been explored. In addition, our Studies showed that the contributions of $cPLA_{2\alpha}$, 5-LO and LTs to microbial traversal of the blood-brain barrier are likely to occur via activation of protein kinase C (PKC).

The data herein indicates that host cell $cPLA_{2\alpha}$, 5-LO and LTs contribute to type III GBS and *E. coli* K1 invasion of BMEC monolayers and penetration into the brain, involving PKC. The data also suggests that type III GBS and *E. coli* K1 invade human BMEC monolayers and penetrate into the brain by exploiting specific host cell molecules involving $cPLA_{2\alpha}$.

$cPLA_{2\alpha}$ mediates agonist-induced arachidonic acid release for the production of eicosanoids such as leukotrienes (LTs) (18, 19). LTs comprise one major group of biologically potent lipid mediators and are synthesized from arachidonate by 5-lipoxygenase (5-LO). The enzyme 5-LO, in conjunction with 5-LO-activating protein (FLAP), oxygenates arachidonic acid to leukotriene A4 (LTA4) (19). This unstable intermediate can be hydrolyzed to form the dihydroxyeicosatetraenoate LTB4 or conjugated with glutathione to form the cysteinyl leukotrienes (LTC4, LTD4 and LTE4). The biological actions of LTB4 and cysteinyl LTs are transduced by ligation of specific G-protein coupled receptors (GPCRs), which initiate activation of specific intracellular signaling cascades. The GPCRs for LTB4 have been designated BLT-1 and BLT-2, while those recognizing cysteinyl LTs (LTC4, LTD4 and LTE4) are designated CysLT1 and CysLT2.

Our next studies showed that pretreatment of human BMEC with the CysLT1 antagonist inhibited type III GBS and *E. coli* K1 invasion of human BMEC monolayers. In addition, we showed that *E. coli* K1 penetration into the brain was significantly less in 5-LO-/- mice compared to their strain-matched wild type mice. These findings suggest that host cell 5-LO and cysteinyl LTs are likely to contribute to type III GBS and *E. coli* K1 invasion of human BMEC monolayers and penetration into the brain.

Our additional studies also suggest that inhibitors of 5-LO and FLAP, and CysLT1 antagonists inhibit type III GBS and *E. coli* K1 invasion of human BMEC monolayers. If studies proposed in this application demonstrate that 5-LO inhibitor, FLAP inhibitor and/or CysLT1 antagonists prevent type III GBS and *E. coli* K1 invasion of the blood-brain barrier and penetrations into the brain, then it will be the first novel application of these drugs for prevention of GBS and *E. coli* meningitis.

It is, however, unclear how $cPLA_{2\alpha}$ and LTs contribute to type III GBS and *E. coli* K1 invasion of human BMEC monolayers. Our next Studies showed that type III GBS and *E. coli* K1 activate protein kinase C (PKC), but PKC activation in response to type III GBS and *E. coli* K1 was decreased in the presence of $cPLA_{2\alpha}$ inhibitor. These findings suggest for the first time that the contributions of $cPLA_{2\alpha}$ and LTs to type III GBS and *E. coli* K1 invasion of human BMEC monolayers are likely to involve PKC.

Additional Studies

A. Development of the In Vitro Blood-Brain Barrier Model by Isolation and Cultivation of Human Brain Microvascular Endothelial Cells (HBMEC).

HBMEC were isolated from small fragments of cerebral cortex as described previously (11-14). Briefly, brain specimens devoid of large blood vessels were homogenized in DMEM containing 2% bovine calf serum (DMEM-S) and centrifuged in 15% dextran in DMEM-S for 10 minutes at 1000×g. The pellets containing crude microvessels were further digested in a solution containing collagenase/dispase (1 mg/ml) for 1 hr at 37° C. Microvascular capillaries were isolated by adsorption to a column of glass beads and washing off the beads, and recovered in growth medium. Cell viability was greater than 95% as judged by trypan blue exclusion test. The human brain microvessels were plated on collagen coated dishes or glass coverslips and cultured in RPMI 1640 based growth medium at 37° C. in a humid atmosphere of 5% $CO_2$.

The resulting HBMEC were positive for factor VIII, carbonic anhydrase IV, *Ulex Europaeus* Agglutinin I, took up acetylated low-density lipoprotein (AcLDL) and expressed gamma-glutamyl transpeptidase, demonstrating their brain endothelial characteristics. HBMEC were purified by FACS using fluorescently labeled DiI-AcLDL and found to be >99% pure after studying non-endothelial cell types using markers for astrocyte, oligoglia, pericyte, epithelial cell, and microglia as well as by studying the morphology for fibroblast contamination. These HBMEC were split in a ratio of 1:3 twice a week using trypsin/EDTA and cultured without losing their specific characteristics up to passage 13.

Upon cultivation on collagen-coated Transwell inserts these HBMEC exhibited morphologic and functional properties of tight junction formation as well as polar monolayer. These are shown by our demonstrations of tight junction proteins (such as ZO-1) and adherens junction proteins (such as β-catenin) and their spatial separation, limited transendothelial permeability to inulin (m.w. 4,000 Da), and development of high transendothelial electrical resistance (11-14), a unique property of the brain microvascular endothelial monolayer.

Figure 20:
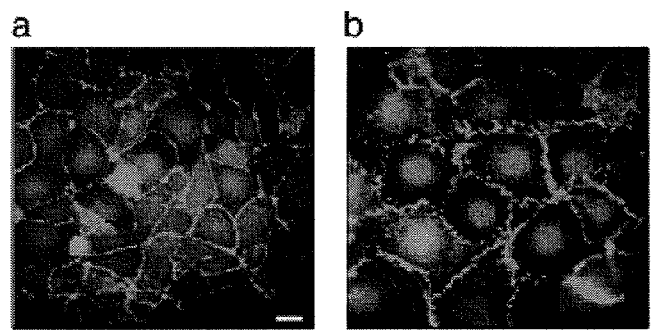
FIG. 20 shows an immunofluorescence demonstration of (a) tight junction protein (ZO-1) and (b) adherens junction protein (β-catenin) in primary HBMEC monolayers. Scale bar=40 µm.

FIG. 20 shows the demonstrations of ZO-1 and β-catenin in HBMEC. Briefly, primary HBMEC grown on cover slips were fixed in 4% paraformaldehyde and then permeabilized with 0.2% Triton X-100. The cells were incubated with primary antibody against ZO-1 or β-catenin, followed by Alexa fluor conjugated secondary antibody, and mounted onto the stage of a fluorescent microscope.

B. GBS and *E. coli* K1 Association with and Invasion of Human BMEC.

Our next experiment was to examine clinical isolates of GBS and *E. coli* K1 strains commonly associated with neonatal meningitis for their ability to associate with and invade human BMEC as previously described (15, 16).

GBS. Logarithmic phase cultures of GBS grown in Todd-Hewitt broth at 37° C. were washed and suspended in tissue culture medium. Approximately $5 \times 10^5$ CFUs of GBS were added to confluent human BMEC grown in each well of a 24-well plate (Corning Costar, multiplicity of infection of 5 bacteria/cell). The plates were centrifuged at 800×g for 10 min to promote the contact of GBS to the surface of the human BMEC monolayer, and then they were incubated for 2 hr at 37° C. The monolayers were washed three times with PBS and incubated with medium containing gentamicin (100

μg/ml) and penicillin (5 μg/ml) at 37° for 2 hr to kill extracellular bacteria. The monolayers were washed again, lysed, and viable intracellular bacteria were enumerated by culturing onto sheep blood agar plates. The percent invasion was calculated as (the number of intracellular bacteria divided by the number of bacteria inoculated)×100. Each assay was run in triplicate and also repeated at least twice. In one set of experiments the total GBS associated with human BMEC were quantified by the above procedure except that the incubation with gentamicin/penicillin was omitted. The results are shown in FIG. 21.

Figure 21:
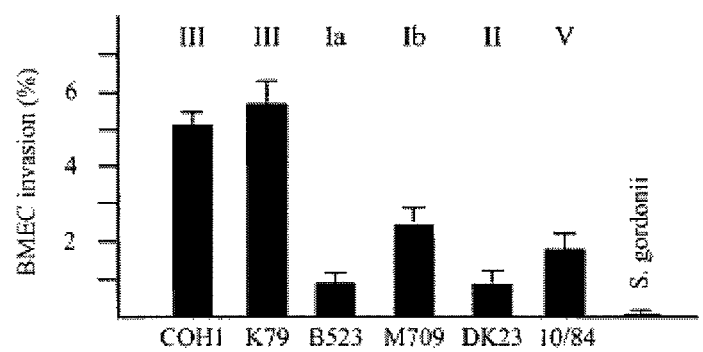
FIG. 21 shows HBMEC invasion (%) by GBS strains, representing the capsular serotypes (Ia, Ib, II, III, and V) commonly associated with neonatal sepsis and meningitis (mean±SD). *Streptococcus gordonii* was used as a negative control.

As shown in FIG. 21, all GBS strains are shown to invade human BMEC monolayers, whereas the negative control *Streptococcus gordonii* strain was non-invasive (16). Of interest, the two type III isolates (strains COH1 and K79) invaded human BMEC more efficiently (5 to 6% of the original inoculum) than strains belonging to the other capsular serotypes (1 to 2.5%). Similarly, total human BMEC-associated GBS were greater for type III strains than for the other capsular serotypes, and approximately 30% of total human BMEC-associated GBS were shown to have invaded the intracellular compartment within the 2 hr-incubation period.

It is important to point out that all GBS strains showed similar growth rates in the above tissue culture medium and also did not affect the human BMEC viability, as determined by live/dead stain (Molecular Probes).

*E. coli.* Human BMEC association and invasion assays were carried out as described previously (15). Briefly, for association assays, confluent human BMEC in 24-well tissue culture plates were incubated with $10^7$ CFU of *E. coli* at a multiplicity of infection of 100 for 90 minutes at 37° C. The monolayers were washed three times with PBS, lysed with sterile water, and the released bacteria were enumerated by plating on sheep blood agar plates. Results were calculated as a percent of the initial inoculum and expressed as percent relative association compared to percent association of the parent strain RS 218.

For invasion assays, human BMEC monolayers were incubated with $10^7$ CFU of *E. coli* for 90 minutes as described above. The monolayers were washed once and then incubated with experimental medium containing gentamicin (100 μg/ml) for 1 hour to kill extracellular bacteria. The monolayers were washed, lysed, and released internalized bacteria were enumerated as described above. Results were calculated as a percent of the initial inoculum and expressed as percent relative invasion compared to percent invasion of the parent *E. coli* K1 strain RS 218.

The parent *E. coli* K1 strain RS218 exhibited the human BMEC association and invasion frequencies (mean±SD) of 20±9% and 0.3±0.2%, respectively. The association frequencies represent the total number of bacteria bound to and internalized into human BMEC, but internalized bacteria represent approximately 1% of the total associated bacteria. These findings indicate that the bacteria bound to HBMEC represent almost all of the total associated bacteria, and the human BMEC association and binding frequencies were used interchangeably for *E. coli* K1.

C. The Role of $cPLA_{2\alpha}$ in Microbial Invasion of Human BMEC and Penetration into the Brain.

We next showed that host cell $cPLA_{2\alpha}$ contributes to type III GBS and *E. coli* K1 invasion of human BMEC monolayers, using pharmacological inhibition of $cPLA_{2\alpha}$ (using AACOCF3) as described previously (24). Briefly, human BMEC were pretreated with AACOCF3 for 60 min, and then processed for type III GBS and *E. coli* K1 binding and invasion assays, as described above. The results are shown in FIG. 22.

Figure 22:
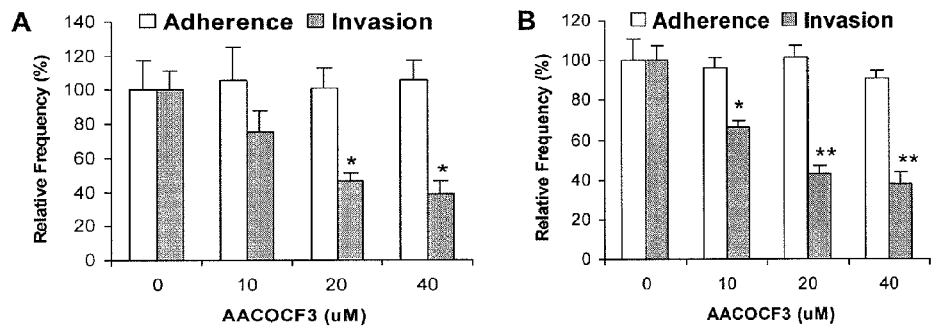
FIG. 22 shows pretreatment of human BMEC with AACOCF3 (an inhibitor of cPLA2α) for 60 mins inhibited (A) type III GBS strain K79 invasion and (B) *E. coli* K1 strain RS218 invasion in a dose-dependent manner, while it did not affect their binding to human BMEC. Data shown are mean±SEM of two separate experiments. Each experiment was performed in triplicate. *P<0.05; **P<0.01, compared to vehicle control (0.15% ethanol).

As shown in FIG. 22, AACOCF3 exhibited a dose-dependent inhibition of type III GBS and *E. coli* K1 invasion of human BMEC, while it failed to affect type III GBS and *E. coli* K1 binding to human BMEC. It is important to note that AACOCF3 at 40 μM did not affect the integrity of the human BMEC monolayers, as determined by live/dead stain (Molecular probes), and also did not affect growth of type III GBS and *E. coli* K1 during the experimental period, as determined by comparing CFUs in the presence or absence of AACOCF3 in experimental medium.

In contrast, inhibitors of $Ca^{2+}$-independent $PLA_2$ ($iPLA_2$) and $Ca^{2+}$-dependent secretory $PLA_2$ ($sPLA_2$) (e.g., bromoenol lactone and 12-episcalaradial, respectively) did not exhibit any significant inhibition on GBS and *E. coli* invasion of human BMEC (1-3, 24).

We next examined the roles of $cPLA_{2\alpha}$ in type III GBS and *E. coli* K1 penetrations into the brain by studying $cPLA_{2\alpha}-/-$ mice as compared to their strain-matched wild type mice (BALB/c).

Type III GBS. Each animal received $10^7$ CFU of type III GBS strain K79 in 100 μl PBS via the tail vein. One hour later, the blood specimens were obtained for CFU determination, and the animals perfused with sterile Ringer's solution until the perfused solution became colorless. The brains, kidneys and spleens were removed, weighed, homogenized and cultured for determinations of CFUs. The results are shown in FIG. 23.

Figure 23:
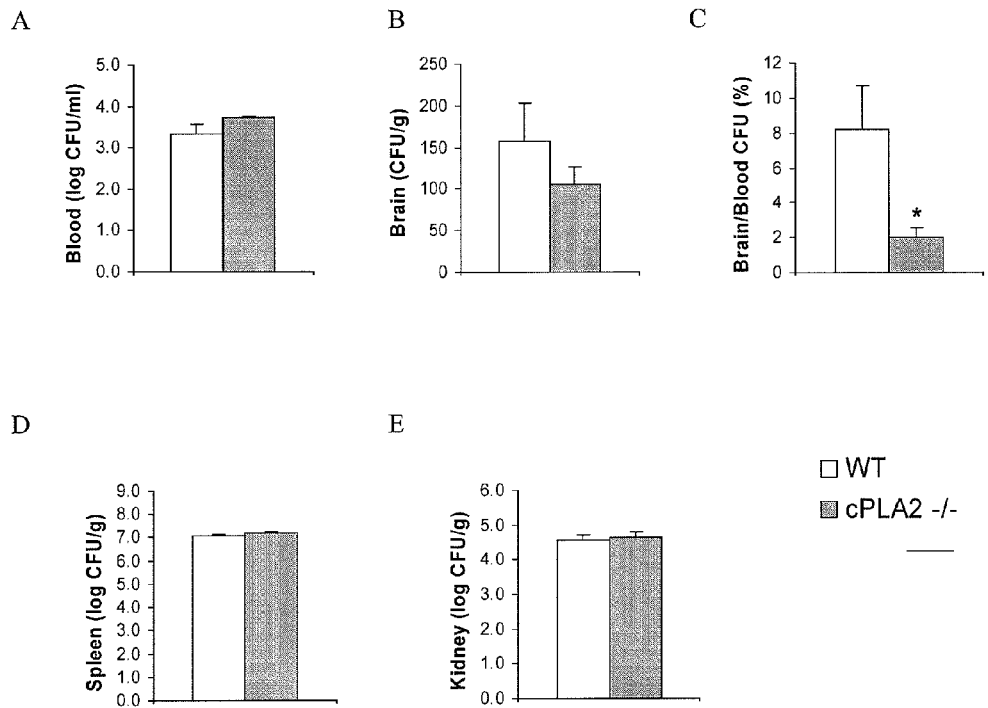
FIG. 23 shows type III GBS penetration into brain, expressed as CFU/gm of brain and [(brain CFUs/gm)/(blood CFUs of ml)]×100, is significantly less in $cPLA_{2\alpha}$-/- mice compared to their wild type mice. In contrast, CFUs recovered from the blood, kidneys and spleens did not differ significantly between the two groups of $cPLA_{2\alpha}$, -/- and wild type mice. Data shown are mean±SEM. *P<0.05, between wild type (WT, n=7) and cPLA2 knockout mice (n=7).

As shown in FIG. 23, the bacterial counts recovered from the brain (CFU/gm of brain) were significantly less in $cPLA_{2\alpha}-/-$ mice than in wild type mice ($p<0.05$) (4B). GBS penetration into the brain is shown to depend on the magnitude of bacteremia (1-3, 7), and GBS penetration into the brain was also expressed as [(CFUs/gm of brain)/(CFUs of ml of blood)]×100, which was significantly less in $cPLA_{2\alpha}-/-$ mice compared to the wild type mice (4C). Thus, the penetration defect into the brain of $cPLA_{2\alpha}-/-$ mice was not the result of decreased levels of bacteremia compared to the wild type mice (in fact, bacterial counts in the blood were somewhat higher in $cPLA_{2\alpha}-/-$ mice than in wild type mice) (23A). These findings suggest that type III GBS penetration into the brain is impaired by deletion of host cell $cPLA_{2\alpha}$.

Of interest, the bacterial counts recovered from the spleens and kidneys (CFUs/gm) did not differ between the two groups of animals (CFUs were slightly higher in $cPLA_{2\alpha}-/-$ mice than in wild type mice) (23C and 23D).

Taken together, these findings indicate that $cPLA_{2\alpha}$ is likely to contribute to type III GBS penetration, specifically into the brain.

*E. coli* K1. Each animal received $10^7$ CFU of *E. coli* K1 strain RS218 via the tail vein. One hour later, the blood specimens were obtained for CFU determination, and the animals perfused, and the brains, kidneys and spleens were removed for determinations of CFUs as described above for GBS. The results are shown in FIG. 24.

Figure 24:
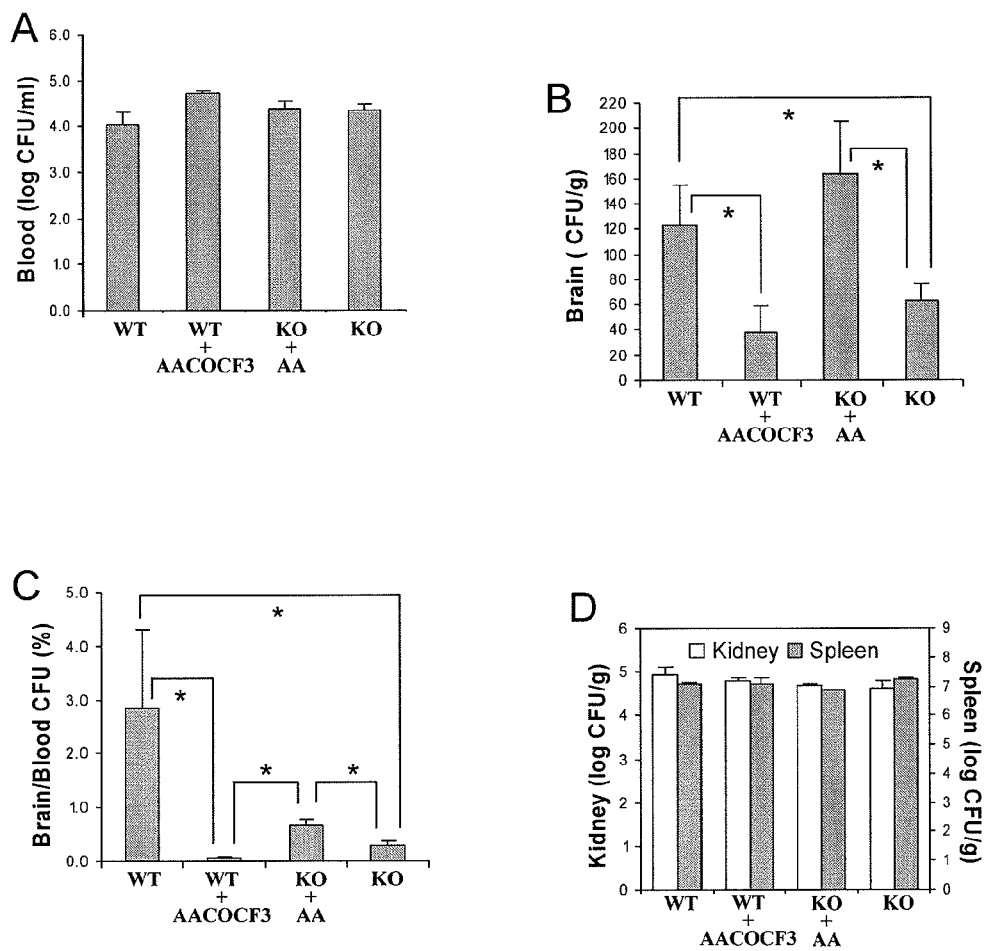
FIG. 24 shows *E. coli* K1 penetration into the brain was significantly less in cPLA2α-/- mice (KO) compared to their wild type (WT) (B & C). AACOCF3 (cPLA2α inhibitor) inhibited *E. coli* penetration into the brain of wild type mice (B & C), while arachidonic acid (AA) rescued the decreased *E. coli* penetration into the brain of cPLA2α-/- mice (B & C). In contrast, the bacterial counts in the blood, kidney and spleen did not differ between experiments groups of cPLA2α-/- and wild type mice (A & D). Data represent mean±SEM of 3-12 animals per group. *p<0.05

As shown in FIG. 24, bacterial counts recovered from the brains and percent of brain CFUs relative to blood CFUs were significantly less ($p<0.05$) in $cPLA_{2\alpha}-/-$ mice compared to wild type animals (B and C). In contrast, bacterial counts in the blood (CFU/ml) were similar between $cPLA_{2\alpha}-/-$ and their wild type animals (FIG. 5A). These findings indicate that decreased *E. coli* penetration into the brain of $cPLA_{2\alpha}-/-$ is not the result of decreased levels of bacteremia.

*E. coli* K1 penetrations into the kidneys and spleens (CFU/gm) did not differ between $cPLA_{2\alpha}-/-$ and wild type mice. These findings suggest that $cPLA_{2\alpha}$ is likely to contributes to *E. coli* K1 penetration, specifically into the brain.

To further verify the role of cPLA$_{2\alpha}$ in *E. coli* K1 penetration into the brain, we showed that intravenous administration of AACOCF3 (cPLA$_{2\alpha}$ inhibitor, 4 mM in 50 μl PBS, the concentration which inhibits cPLA$_{2\alpha}$ in mice, 25) 30 mins before bacterial injection significantly (p<0.05) decreased *E. coli* K1 penetration into the brain of wild type mice to the level observed in cPLA$_{2\alpha}$-/- mice (FIGS. 24 B & C).

The enzyme cPLA$_{2\alpha}$ prefers arachidonic acid as the sn-2 fatty acyl moiety of its phospholipids substrate (18). We next showed that exogenous administration of arachidonic acid (1.2 μg/mouse in 50 μl PBS intravenously) 30 mins before bacterial injection significantly enhanced *E. coli* K1 penetration into the brain in cPLA$_{2\alpha}$-/- mice to the level observed in the wild type mice (FIGS. 24 B & C), but did not affect the bacterial counts in the blood, kidney and spleen compared to the vehicle control (FIGS. 24 A & D). The enhancement of *E. coli* K1 penetration into the brain of cPLA$_{2\alpha}$-/- mice by arachidonic acid, however, was not accompanied by any changes in the blood-brain barrier permeability, as shown by no significantly increased extravasation of intravenously administered Evans blue dye into the brain (see the Experimental Design and Methods). These findings are consistent with those of our in vitro studies, where *E. coli* K1 traversal of the human BMEC monolayers did not result in any change in the integrity of HBMEC monolayers (12).

Taken together, these findings demonstrate for the first time the novel role of host cell cPLA$_{2\alpha}$ in *E. coli* and type III GBS invasion of the human BMEC monolayers and penetration into brain.

These findings also suggest for the first time that inhibition of host cell signaling molecules involved in BMEC invasion and CNS penetration provides a novel concept and approach in our strategies for prevention of *E. coli* and GBS penetration into the CNS, an essential step for the development of meningitis, as shown here with both gene deletion and pharmacological inhibition of cPLA$_{2\alpha}$.

5-LO and CysLTs. cPLA$_{2\alpha}$ mediates agonist-induced arachidonic acid release for production of eicosanoids such as leukotrienes (LTs) (18, 19). LTs comprise one major group of biologically potent lipid mediators and are synthesized from arachidonate by 5-LO.

We next examined whether 5-LO contributes to *E. coli* K1 penetration into the brain by studying 5-LO-/- mice (129SvEv background) as compared to strain-matched wild type mice by the methods described above with cPLA$_{2\alpha}$-/- mice. The results are shown in FIG. 25.

Figure 25:
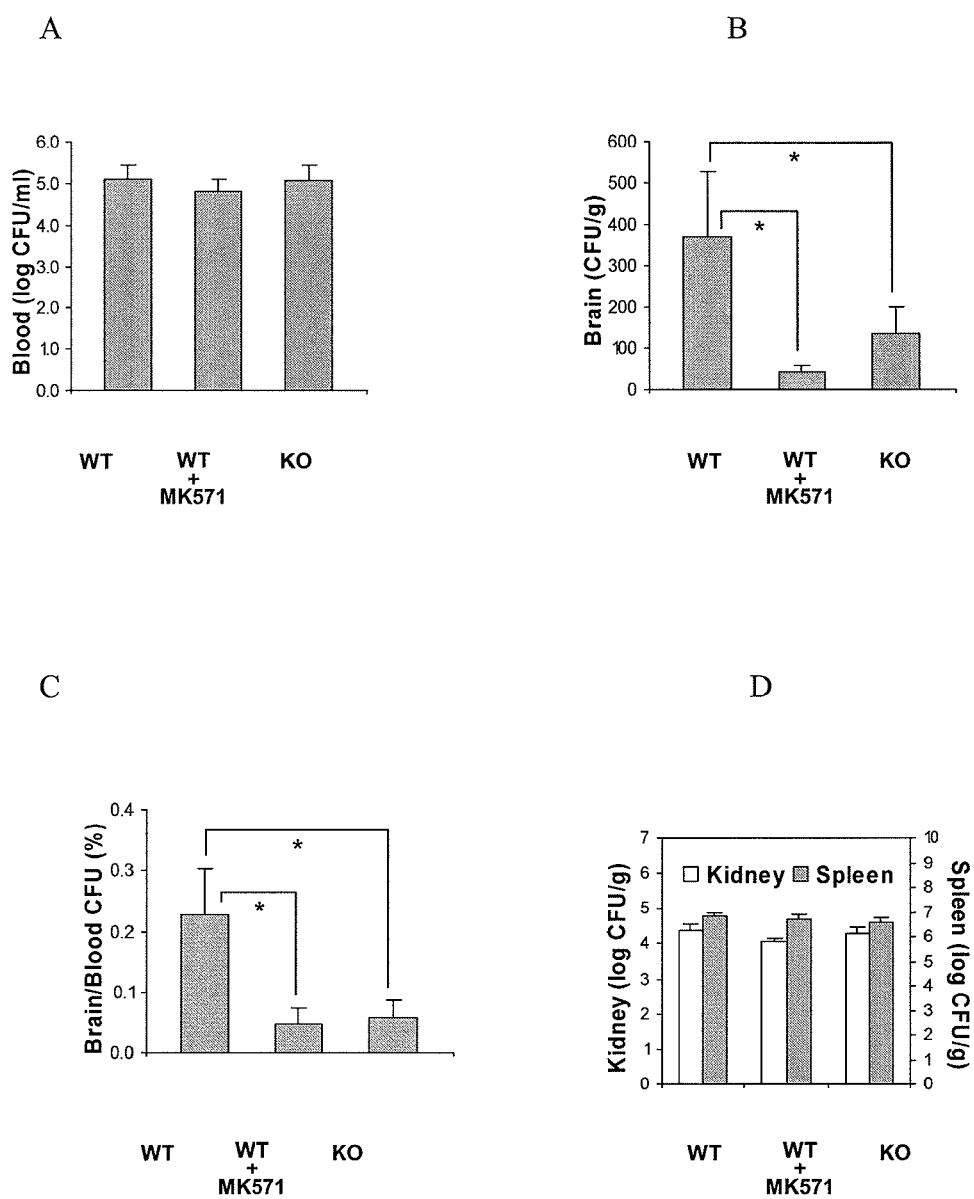
FIG. 25 shows *E. coli* K1 penetration into the brain was significantly less in 5-LO-/- mice (KO) compared to their wild type (WT) (B & C). In contrast, the bacterial counts in the blood, kidney and spleen did not differ between the two groups (A & D). Administration of MK571 (CysLT1 antagonist) before bacterial injection significantly decreased *E. coli* penetration into the brain of the wild type mice (B & C). Data represent mean±SEM of 3-7 animals per group. *p<0.05

As shown in FIG. 25, bacterial counts recovered from the brain and percent of brain CFUs relative to blood CFUs were significantly less (p<0.05) in 5-LO-/- mice compared to wild type animals (25B and C), while bacterial counts in the blood, kidney and spleen were similar between 5-LO-/- and their wild type animals (25A and D). These findings indicate that 5-LO is likely to contribute to *E. coli* K1 penetration specifically into the brain.

The enzyme 5-LO, in conjunction with 5-LO-activating protein (FLAP), oxygenates arachidonic acid to LTA4. This unstable intermediate can be hydrolyzed to form the LTB4 or conjugated with glutathione to form the cysteinyl LTs (LTC4, LTD4 and LTE4) (19). The biological actions of LTB4 and cysteinyl LTs are transduced by ligation of specific G-protein coupled receptors (GPCRs), which initiate activation of specific intracellular signaling cascades. The GPCRs for LTB4 have been designated BLT-1 and BLT-2, while those recognizing cysteinyl LTs are designated CysLT1 and CysLT2 (19).

We next examined which LTs are involved in *E. coli* K1 invasion of human BMEC monolayers and penetration into the brain by using MK571 (the CysLT1 antagonist) and CP105696 (the BLT-1 antagonist). Briefly, human BMEC were pretreated with MK571 or CP105696 for 30 min and then processed for *E. coli* invasion assays. The results are shown in FIG. 26.

Figure 26:
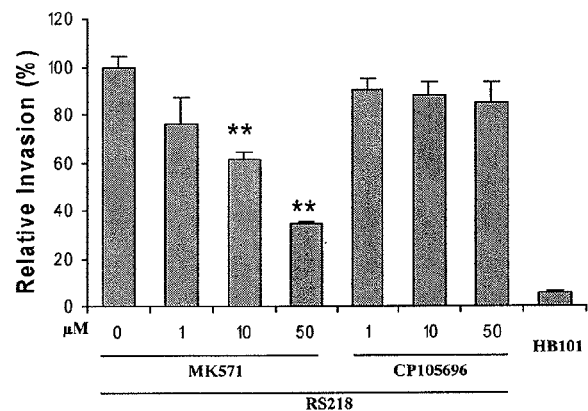
FIG. 26 shows *E. coli* K1 strain RS218 invasion of human BMEC monolayers was inhibited by MK571, but not by CP105696. Data shown are mean±SEM. Each experiment was performed in triplicate. **P<0.01, compared to vehicle control (DMSO).

As shown in FIG. 26, MK571 (the CysLT1 antagonist) inhibited *E. coli* K1 invasion of human BMEC monolayers in a dose-dependent manner, while CP105696 (the BLT-1 antagonist) failed to affect *E. coli* K1 invasion of human BMEC monolayers. These findings indicate that cysteinyl LTs, not LTB4, are involved in *E. coli* K1 invasion of human BMEC monolayers.

We next examined the effect of MK571 on *E. coli* K1 penetration into the brain. Oral administration of MK571 (400 μg/mouse in 150 μl PBS) one hour before bacterial injection significantly decreased *E. coli* K1 penetration into the brain in the wild type mice to the level observed in 5-LO-/- mice (FIGS. 25B and C), but did not affect the bacterial counts in the blood, spleen and kidney compared to the vehicle control (FIGS. 25A and D). These findings demonstrate for the first time that cysteinyl LTs are likely to contribute to *E. coli* K1 penetration into the CNS, the essential step in the development of *E. coli* meningitis.

Figure 27:
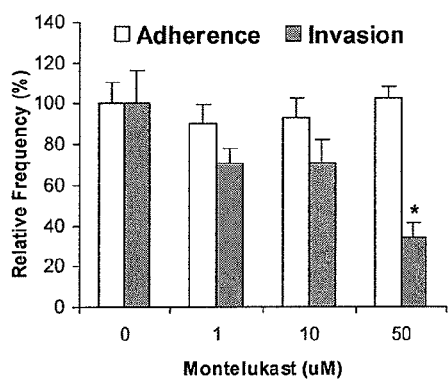
FIG. 27 shows pretreatment of human BMEC with montelukast (the CysLT1 antagonist) inhibited (A) type III GBS strain K79 invasion and (B) *E. coli* K1 strain RS218 invasion in a dose-dependent manner, while it did not affect their binding to human BMEC. Data shown are mean±SEM of two separate experiments. Each experiment was performed in triplicate. *P<0.05; **P<0.01, compared to vehicle control (DMSO).
Figure 27:
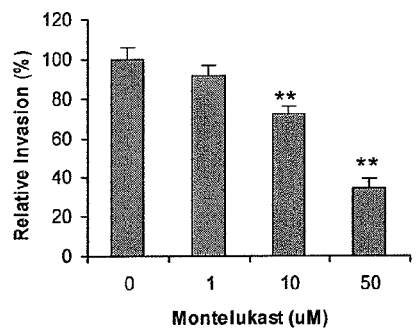

We next examined the effect of montelukast on type III GBS and *E. coli* K1 invasion of human BMEC by the methods described earlier. Briefly, human BMEC were treated with monelukast for 60 min and then processed for binding and invasion assays with type III GBS strain K79 and *E. coli* K1 strain RS 218. The results are shown in FIG. 27.

If the information derived from our application supports that 5-LO and FLAP inhibitors and CysLT1 antagonists prevent GBS and *E. coli* penetration into the CNS, then it will be the first novel application of these drugs for prevention and therapy of GBS and *E. coli* meningitis.

Taken together, these findings indicate that inhibition and/or blockade of the host cell molecules involved in GBS and *E. coli* invasion of human BMEC monolayers provides a novel concept and approach in our strategies for prevention and therapy of GBS and *E. coli* meningitis.

G. cPLA$_{2\alpha}$, 5-LO and Cysteinyl LTs Contribute to Activation of PKC in Response to Type III GBS and *E. coli* K1 in HBMEC.

Our studies so far indicate that host cell cPLA$_{2\alpha}$, 5-LO and cysteinyl LTs are involved in type III GBS and *E. coli* K1 invasion of BMEC monolayers.

We have previously shown that RhoGTPases and PKC contribute to type III GBS and *E. coli* K1 invasion of BMEC monolayers (1-3), and our next studies were to examine whether cPLA$_{2\alpha}$ activations are related to RhoGTPases and PKC in type III GBS and *E. coli* K1 invasion of human BMEC monolayers (e.g., up- and down-stream of each other) by using inhibitors of cPLA$_{2\alpha}$ (AACOCF3), Rho kinase (Y-27632), Rac1 (NSC-23766) and PKC (calphostin C). As expected, AACOCF3, Y-27632, NSC-23766 and calphostin C inhibited type III GBS and *E. coli* K1 invasion of human BMEC monolayers in a dose-dependent manner (1-3). Of interest, pretreatment with AACOCF3 inhibited PKC activation, while inhibitors of Rho kinase, Rac1 and PKC did not exhibit any inhibition of other signaling molecules, suggesting that cPLA$_{2\alpha}$, 5-LO and cysteinyl LTs may be upstream of PKC in response to type III GBS and *E. coli* K1 in human BMEC monolayers H. Summary.

Using our innovative in vitro blood-brain barrier model, we have shown that type III GBS and *E. coli* K1 strains invade human BMEC, and that type III GBS and *E. coli* K1 invasion of human BMEC monolayers and penetration into the brain can involve cPLA$_{2\alpha}$, 5-LO and cysteinyl LTs. Our studies also showed that cPLA$_{2\alpha}$, 5-LO and cysteinyl LTs contribute to type III GBS and *E. coli* K1 invasion of human BMEC monolayers via PKCα activation.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

LITERATURE CITED

Kim K S: Effect of antimicrobial therapy for experimental infections due to group B *streptococcus* on mortality and clearance of bacteria. J. Infect. Dis. 155:1233-1241, 1987.

Kim K S, Neurological diseases: pathogenesis of bacterial meningitis: from bacteremia to neuronal injury. Nature Rev. Neuroscience 4:376-385, 2003.

Kim K S. Mechanisms of microbial traversal of the blood-brain barrier. Nature Rev Microbiol 6:625-634, 2008

McCracken G H, JR., Threlkeld N, Mize S, Baker C J, Kapal S L, Fraingezicht I, Feldman W F, Schad U and The Neonatal Meningitis Cooperative Study Group. Moxalactam therapy for neonatal meningitis due to gram-negative sepsis enteric bacilli. JAMA 252:1427-32, 1984.

Kim K S. Comparison of cefotaxime, imipenem-cilastatin, ampicillin-gentamicin and ampicillin-chloramphenicol in the treatment of experimental *Escherichia coli* bacteremia and meningitis. Antimicrob Agents Chemother 28:433-36, 1985.

Dietzman D E, Fischer G W, Schoenknecht F D. Neonatal *Escherichia coli* septicemia-bacterial counts in blood. J Peds 85:128-30, 1974.

Ferrieri P, Burke B, and Nelson, J. Production of bacteremia and meningitis in infant rats with group B streptococcal serotypes. Infect. Immun. 27:1023-1032, 1980.

Doran K S, Engelson E J, Khosravi A, Miasy H C, Fedke I, Equils O, Michelsen K S, Arditi M, Peschel A, Nizet V. Blood-brain barrier invasion by group B *streptococcus* depends upon proper cell-surface anchoring of lipoteichoic acid. J Clin Invest 115:2499-2507, 2005

Kim K S, Itabashi H, Gemski P, Sadoff J, Warren R L, Cross A S. The K1 capsule is the critical determinant in the development of *Escherichia coli* meningitis in the rat. J. Clin. Invest. 90:897-905, 1992.

Berman P H and Banker B Q. Neonatal meningitis. A clinical and pathological study of 29 cases. Pediatrics 38:6-24, 1966.

Stins M F, Gilles F, and Kim K S: Selective expression of adhesion molecules on human brain microvascular endothelial cells. J. Neuroimmunol. 76:81-90, 1997.

Stins M F, Badger J L, and Kim K S. Bacterial invasion and transcytosis in transfected human brain microvascular endothelial cells. Microb. Pathogenesis 30:19-28, 2001.

Ruffer C, Strey A, Janning A, Kim K S, and Gerke V. Cell-cell junctions of dermal microvascular endothelial cells contain tight and adherens junction proteins in spatial proximity. Biochemistry 43:5360-5369, 2004.

Kim Y V, DiCello F, Hillaire C S, and Kim K S. Protease-activated receptors of human brain microvascular endothelial cells: Expression and differential Ca$^{2+}$ signaling induced by thrombin and protease-activated receptor-1 activating peptide. Am. J. Physiol. Cell Physiol. 286:C31-42, 2004

Huang S H, Wass C A, Fu Q, Prasadarao N V, Stins M, Kim K S. *E. coli* invasion of brain microvascular endothelial cells in vitro and in vivo: Molecular cloning and characterization of *E. coli* invasion gene ibe10. Infect. Immun. 63:4470-75, 1995.

Nizet V, Kim K S, Stins M, Jonas M, Nguyen D, and Rubens C E. Invasion of brain microvascular endothelial cells by group B streptococci. Infect. Immun. 65:5074-5081, 1997.

Nemani P V, Stins M, Wass C A, Shimada H and Kim K S. Outer membrane A promoted cytoskeletal rearrangement of brain microvascular endothelial cells is required for *E. coli* invasion. Infect Immun 67: 5775-5783, 1999.

Ghosh M, Tucker D E, Burchett S A, Leslie C C. Properties of the group IV phospholipase A2 family. Prog Lipid Res 45:487-510, 2006

Peters-Golden M, Henderson W R. Leukotrienes. N Eng J Med 357:1841-1854, 2007

Levy O. Innate immunity of the newborn. Nar Rev Immunol 7:379-390, 2007

Rubin L L and Staddon J M. The cell biology of the blood-brain barrier. Annu Rev. Neurosc 22:11-28, 1999.

Cossart P and Sansonetti P J. Bacterial invasion: the paradigms of enteroinvasive pathogens. Science 304:242-8, 2004.

Knodler L A, Celli J and Finlay B B. Pathogenic trickery: deception of host cell processes. Nat. Rev. Mol. Cell. Biol. 2:578:88, 2001.

Das A, Asatryan L, Reddy M A, Wass C A, Stins M, Joshi S, Bonentre J V, Kim K S. Differential role of cytosolic phospholipase A2 in the invasion of brain microvascular endothelial cells by *Escherichia cells* and *Listeria monocytogenes*. J Infect Dis 184:732-37, 2001.

Kalyvas A, David S. Cytosolic phospholipase A2 plays a key role in the pathogenesis of multiple sclerosis-like disease. Neuron 2004; 41:323-335.

Montuschi P, Sala A, Dahlen S, Folco G. Pharmacological modulation of the leukotriene pathways in allergic airways disease. Drug Discovery Today 12:404-412, 2007.

Capra V, Thompson M D, Sala A, Cole D E, Folco G, Rovati G E. Cysteinyl leukotrienes and their receptors in asthma and other inflammatory diseases: critical update and emerging trends. Med Res Rev 27:469-527, 2007.

Kemp J P. Advances in the management of pediatric asthma: A review of recent FDA drug approvals and label updates. J Asthma 42:615-622, 2005.

Coyne C B, Kim K S, Bergelson J M. Poliovirus entry into human brain microvascularendothelial cells requires receptor-induced activation of SHP-2. EMBO J 26:4016-4028, 2007

Qiao J, Huang F, Naikawadi R P, Kim K S, Said T, Lum H. Lysophosphatidylcholine impairs endothelial barrier function through the G-protein coupled receptor, GPR4. Am J Physiol Lung Cell Mol Physiol. 291:L91-L101, 2006

Mukherjee A, Morosky S A, Shen L, Weber C R, Turner J R, Kim K S, Wang T, Coyne C B. Retinoic-acid induced gene (RIG-I) associates with the actin cytoskeleton via CARD-dependent interactions. J Biol Chem 284:6486-6494, 2009

Stins, M, Pearce D, DiCello F, Erdreich-Epstein A, Pardo C and Kim K S. Induction of ICAM-1 on human brain endothelial cells by HIV-1 gp120: role of CD4 and chemokine co-receptors. Lab Invest 83:1787-1798, 2003.

Stins M, Pearce D, Choi H, DiCello F, Pardo C and Kim K S. CD4 and chemokine receptors on human brain microvascular endothelial cells, implications for HIV-1 pathogenesis. Endothelium 11:1-10, 2004.

Pavicevic Z, Leslei C C, Malik K U. cPLA2 phosphorylation at serine-515 and serine-505 is required for arachidonic acid release in vascular smooth muscle cells. J Lipid Res 49:724-737, 2008

Hefner Y, Borsch-Haubold A G, Murakami M, Wilde J I, Pasquet S, Schieltz D, Ghomashchi F, Yates J R, Armstrong C G, Paterson A, Cohen P, Fukunaga R, Hunter T, Kudo I, Watson S P, Gelb M H. Serine 727 phosphorylation and activation of cytosolic phosholipase A2 by MNK1-related protein kinases. J Biol Chem 275:37542-37551, 2000

Tian W, Wijewickrama G T, Kim J H, Das S, Tun M P, Gokhale N, Jung J W, Kim K P, Cho W. Mechanism of regulation of group IVA phospholipase A2 activity by serine 727 phosphorylation. J Biol Chem 283:3960-3971, 2008

Shin S, Kim K S. RhoA and Rac1 contribute to type III group B streptococcal invasion of human brain microvascular endothelial cells. Biochem Biophys Res Commun 345: 538-542, 2006

Shin S, Maneesh P, Lee J, Romer L and Kim K S. Focal adhesion kinase is involved in type III group B streptococcal invasion of human brain microvascular endothelial cells. Microb Pathogenesis 41:168-173, 2006

Kaya M, Kayayci R, Kucuk M, Arican N, Elmas I, Kudat H, Korkut F. Effect of losartan on the blood-brain barrier permeability in diabetic hypertensive rats. Life Sci. 73, 3235-44, 2003.

Pu H, Hayashi K, Andras I E, Eum S Y, Henning B, Toborek M. Limited role of COX-2 in HIV Tat-induced alterations of tight junction protein expression and disruption of the blood-brain barrier. Brain Res. 1184, 333-44, 2007.

Chung J W, Hong S J, Kim K J, Goti D, Stins M F, Shin S, Dawson V L, Dawson T M, Kim K S. 37 kDa laminin receptor precursor modulates cytotoxic necrotizing factor 1-mediated RhoA activation and bacterial uptake. J Biol Chem 278:16857-16862, 2003

Benjamin, C. F., C. Canetti, F. Q. Cunha, S. L. Kunkel, and M. Peters-Golden. 2005. Opposing and hierarchical roles of leukotrienes in local innate immune versus vascular responses in a model of sepsis. J. Immunol. 174:1616-1620.

Berman, P. H., and B. Q. Banker. 1966. Neonatal meningitis. A clinical and pathological study of 29 cases. Pediatrics 38:6-24.

Capra, V., M. D. Thompson, A. Sala, D. E. Cole, G. Folco, and G. E. Rovati. 2007. Cysteinyl-leukotrienes and their receptors in asthma and other inflammatory diseases: critical update and emerging trends. Med. Res. Rev. 27:469-527.

Das, A., L. Asatryan, A. Reddy, C. A. Wass, M. F. Stins, S. Joshi, J. V. Bonventre, and K. S. Kim. 2001. Differential role of cytosolic phospholipase A2 in the invasion of brain microvascular endothelial cells by *Escherichia coli* and *Listeria monocytogenes*. J. Infect. Dis. 184:732-737.

Dietzman, D. E., G. W. Fischer, and F. D. Schoenknecht. 1974. Neonatal *Escherichia coli* septicemia—bacterial counts in blood. J. Pediatr. 85:128-130.

Evans, J. F., A. D. Ferguson, R. T. Mosley, and J. H. Hutchinson. 2008. What's all the FLAP about?: 5-lipoxygenase-activating protein inhibitors for inflammatory diseases. Trends Pharmacological Sci. 29:72-78.

Funk, C. D. 2005. Leukotriene modifiers as potential therapeutics for cardiovascular disease. Nat. Rev. Drug Discov. 4:664-672.

Ghosh, M., D. E. Tucker, S. A. Burchett, and C. C. Leslie. 2006. Properties of the group IV phospholipase A2 family. Prog. Lipid Res. 45:487-510.

Huang, S. H, C. A. Wass, Q. Fu, N. V. Prasadarao, M. Stins, and K. S. Kim. 1995. *E. coli* invasion of brain microvascular endothelial cells in vitro and in vivo: Molecular cloning and characterization of *E. coli* invasion gene ibe10. Infect. Immun. 63:4470-4475.

Huang, S. H., Y. H. Chen, Q. Fu, Y. Wang, M. Stins, C. Wass, and K. S. Kim. 1999. Identification and characterization of an *E. coli* invasion gene locus ibeB required for penetration of brain microvascular endothelial cells. Infect. Immun. 67:2103-2109.

Kandzari, D. E., J. Chen, and P. J. Goldschmidt-Clermont. 2006. Regulation of the actin cytoskeleton by inositol phospholipids pathways. Subcell. Biochem. 26:97-114.

Kaya, M., R. Kalayci, M. Küçük, N. Arican, I. Elmas, H. Kudat, and F. Korkut. 2003. Effect of losartan on the blood-brain barrier permeability in diabetic hypertensive rats. Life Sci. 73:3235-3244.

Kemp, J. P. 2005. Advances in the management of pediatric asthma: a review of recent FDA drug approvals and label updates. J. Asthma. 42:615-622.

Khan, N. A., Y. Wang, K. J. Kim, J. W. Chung, C. A. Wass, and K. S. Kim. 2002. Cytotoxic necrotizing factor-1 contributes to *Escherichia coli* K1 invasion of the central nervous system. J. Biol. Chem. 277:5607-5612.

Kim, K. S. 2001. *Escherichia coli* translocation at the blood-brain barrier. Infect. Immun. 69:5217-5222.

Kim, K. S. 2003. Pathogenesis of bacterial meningitis: from bacteraemia to neuronal injury. Nat. Rev. Neuroscience 4:376-385.

Kim, K. S. 2008. Mechanisms of microbial traversal of the blood-brain barrier. Nat. Rev. Microbiol. 6:625-634.

Kim, K. S., H. Itabashi, P. Gemski, J. Sadoff, R. L. Warren, and A. S. Cross. 1992. The K1 capsule is the critical determinant in the development of *Escherichia coli* meningitis in the rat. J. Clin. Invest. 90:897-905.

Kim, Y., D. Pearce, and K. S. Kim. 2008. Ca2+/Calmodulin-dependent invasion of the human brain microvascular endothelial cells by *Escherichia coli* K1. Cell & Tissue Res 332:427-433.

Kim, Y. V., F. DiCello, C. S. Hillaire, and K. S. Kim. 2004. Protease-activated receptors of human brain microvascular endothelial cells: Expression and differential Ca2+ signaling induced by thrombin and protease-activated receptor-1 activating peptide. Am. J. Physiol. Cell Physiol. 286:C31-42.

Montuschi, P., A. Sala, S. Dahlen, and G. Folco. 2007. Pharmacological modulation of the leukotriene pathway in allergic airway disease. Drug Discovery Today 12:404-412.

Murphy, R. C., and M. A. Gijon. 2007. Biosynthesis and metabolism of leukotrienes. Biochem. J. 405:379-395.

Peters-Golden, M., and W. R. Henderson. 2007. Leukotrienes. N Engl J. Med. 357: 1841-1854.

Pu, H., K. Hayashi, I. E. Andras, S. Y. Eum, B. Hennig, and M. Toborek. 2007. Limited role of COX-2 in HIV Tat-induced alterations of tight junction protein expression and disruption of the blood-brain barrier. Brain Res. 184:333-344.

Ruffer, C., A. Strey, A. Janning, K. S. Kim, and V. Gerke. 2004. Cell-cell junctions of dermal microvascular endothelial cells contain tight and adherens junction proteins in spatial proximity. Biochemistry 43:5360-5369.

Stins, M. F., F. Gilles, and K. S. Kim. 1997. Selective expression of adhesion molecules on human brain microvascular endothelial cells. J. Neuroimmunol. 76:81-90.

Stins, M. F., J. L. Badger, and K. S. Kim. 2001. Bacterial invasion and transcytosis in transfected human brain microvascular endothelial cells. Microb Pathogenesis 30: 19-28.

Wang, Y., S. H. Huang, C. Wass, and K. S. Kim. 1999. The gene locus yijP continues to E. coli K1 invasion of brain microvascular endothelial cells. Infect. Immun. 67:4751-4756.

Zhu, L., D. Schwegler-Berry, V. Castranova, and P. He. 2004. Internalization of caveolin-1 scaffolding domain facilitated by Antennapedia homeodomain attenuates PAF-induced increase in microvessel permeability. Am. J. Physiol. Heart Circ. Physiol. 286:H195-201.

Nemani P V, Stins M, Wass C A, Shimada H and Kim K S. Outer membrane A promoted cytoskeletal rearrangement of brain microvascular endothelial cells is required for E. coli invasion. Infect Immun 67: 5775-5783, 1999.

Kim K S. Escherichia coli translocation at the blood-brain barrier. Infect Immun 2001; 69:5217-5222.

Kim K S. Pathogenesis of bacterial meningitis: from bacteraemia to neuronal injury. Nat Rev Neuroscience 2003; 4:376-385.

Kim K S. Mechanisms of microbial traversal of the blood-brain barrier. Nat Rev Microbiol 2008; 6:625-634.

Berman P H, Banker B Q. Neonatal meningitis. A clinical and pathological study of 29 cases. Pediatrics 1966; 38:6-24.

Kim K S, Itabashi H, Gemski P, et al. The K1 capsule is the critical determinant in the development of Escherichia coli meningitis in the rat. J Clin Invest 1992; 90:897-905

Kim Y V, DiCello F, Hillaire C S, et al. Protease-activated receptors of human brain microvascular endothelial cells: Expression and differential $Ca^{2+}$ signaling induced by thrombin and protease-activated receptor-1 activating peptide. Am J Physiol Cell Physiol 2004; 286:C31-42.

Ruffer C, Strey A, Janning A, et al. Cell-cell junctions of dermal microvascular endothelial cells contain tight and adherens junction proteins in spatial proximity. Biochemistry 2004; 43:5360-5369.

Stins M F, Badger J, Kim K S. Bacterial invasion and transcytosis in transfected human brain microvascular endothelial cells. Micro Pathogenesis 2001; 30:19-28.

Huang S H, Wass C A, Fu Q, et al. E. coli invasion of brain microvascular endothelial cells in vitro and in vivo: Molecular cloning and characterization of E. coli invasion gene ibe10. Infect Immun 1995; 63:4470-4475.

Kalyvas A, David S. Cytosolic phospholipase A2 plays a key role in the pathogenesis of multiple sclerosis-like disease. Neuron 2004; 41:323-335.

Khan N A, Wang Y, Kim K J, et al. Cytotoxic necrotizing factor-1 contributes to Escherichia coli K1 invasion of the central nervous system. J Biol Chem 2002; 277:5607-5612.

Wang Y, Huang S H, Wass C A, et al. The gene locus yijP continues to E. coli K1 invasion of brain microvascular endothelial cells. Infect Immun 1999; 67:4751-4756.

Das A, Asatryan L, Reddy A, et al. Differential role of cytosolic phospholipase A2 in the invasion of brain microvascular endothelial cells by Escherichia coli and Listeria monocytogenes. J Infect Dis 2001; 184:732-737.

Sapirstein A, Saito H, Texel S J, et al. Cytosolic phospholipase A2alpha regulates induction of brain cyclooxygenase-2 in a mouse model of inflammation. Am J Physiol Regul Integr Comp Physiol 2005; 288:R1774-R1782.

Stins M F, Gilles F, Kim K S. Selective expression of adhesion molecules on human brain microvascular endothelial cells. J Neuroimmunol 1997; 76:81-90.

Pu H, Hayashi K, Andras I E, et al. Limited role of COX-2 in HIV Tat-induced alterations of tight junction protein expression and disruption of the blood-brain barrier. Brain Res 2007; 184:333-344.

Kaya M, Kalayci R, Küçük M, et al. Effect of losartan on the blood-brain barrier permeability in diabetic hypertensive rats. Life Sci 2003; 73:3235-3244.

Leslie C C. Properties and regulation of cytosolic phospholipase A2. J Biol Chem 1997; 272:16709-16712.

Ghosh M, Tucker D E, Burchett S A, et al. Properties of the group IV phospholipase A2 family. Prog Lipid Res 2006; 45:487-510.

Ichinose F, Ullrich R, Sapirstein A, et al. Cytosolic phospholipase A(2) in hypoxic pulmonary vasoconstriction. J Clin Invest 2002; 109:1493-1500.

Hegen M, Sun L, Uozumi N, et al. Cytosolic phospholipase A2α-deficient mice are resistant to collagen-induced arthritis. J Exp Med 2003; 197:1297-1302.

Miyaura C, Inada M, Matsumoto C, et al. An essential role of cytosolic phospholipase A2α in prostaglandin E2-mediated bone resorption associated with inflammation. J Exp Med 2003; 197:1303-1310.

Nagase T, Uozumi N, Ishii S, et al. A pivotal role of cytosolic phospholipase A(2) in bleomycin-induced pulmonary fibrosis. Nat Med 2002; 8:480-484.

Nemani P V, Wass C A, Kim K S. Endothelial cell GlcNAcB1-4 GlcNAc epitopes for outer membrane protein A traversal of E. coli across the blood-brain barrier. Infect Immun 1996; 64:154-160.

Fakioglu E, Queenan A M, Bush K, et al. Jenkins S G, Harold B C. AmpC beta-lactamase producing E. coli in neonatal meningitis: diagnostic and therapeutic challenge. J Perinatol 2006; 26:515-517.

Rodríguez-Baño J, Navarro M D, Romero L, et al. Bacteremia due to extended-spectrum beta-lactamase producing E. coli in the CTX-M era: a new clinical challenge. Clin Infect Dis 2006; 43:1407-1414.

I claim:

1. A method for treating a mammal infected by a pathogen selected from the group consisting of Cryptococcus neoformans, E. coli and Group B. Streptococcus to prevent or treat a brain infection consisting essentially of:
   administering to the mammal a therapeutic amount of a compound selected from the group consisting of MK571 and montelukast that inhibits a Cys LT receptor cellular signaling molecule thereby preventing an infection by a pathogen selected from the group consisting of Cryptoccous neoformans, E. coli and Group B Streptococcus from crossing a blood-brain barrier in the mammal.

2. The method of claim 1, wherein the therapeutic amount is from about 0.1 mg/kg to about 100 mg/kg.

3. The method of claim 1, wherein the Cys LT receptor cellular signaling molecule is selected from the group consisting of LTC4, LTD4, and LTE4.

4. The method of claim 1, wherein the mammal in need of treatment for Cryptococcus neoformans has an immuno-compromising disease.

5. The method of claim 4, wherein the immune-compromising disease is HIV or AIDS.

6. The method of claim 1, wherein the subject for Cryptococcus neoformans has a CD4+ T cell count of less than 50 per µl.

7. The method of claim 1, wherein the mammal is a human.

* * * * *

UNITED STATES PATENT AND TRADEMARK OFFICE
CERTIFICATE OF CORRECTION

PATENT NO. : 8,980,917 B2
APPLICATION NO. : 12/997763
DATED : March 17, 2015
INVENTOR(S) : Kwang Kim Page 1 of 1

It is certified that error appears in the above-identified patent and that said Letters Patent is hereby corrected as shown below:

In the Specification

Column 1, Lines 12-15, should read:
STATEMENT OF GOVERNMENTAL INTEREST
This invention was made with government support under NS026310, awarded by the National Institutes of Health. The government has certain rights in the invention.

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*